(12) United States Patent
Despey-Roux et al.

(10) Patent No.: US 7,879,889 B2
(45) Date of Patent: Feb. 1, 2011

(54) THERAPEUTIC USE OF ACYLAMINOTHIAZOLE DERIVATIVES

(75) Inventors: Pierre Despey-Roux, Labarthe sur Leze (FR); Daniel Frehel, Estadens (FR); Bruno Schoentjes, Bois-Guillaume (FR); Viviane Van Dorsselaer, Strasbourg (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/488,658

(22) Filed: Jun. 22, 2009

(65) Prior Publication Data

US 2009/0253753 A1    Oct. 8, 2009

Related U.S. Application Data

(60) Division of application No. 11/186,507, filed on Jul. 21, 2005, now Pat. No. 7,563,903, which is a continuation of application No. PCT/FR2004/000140, filed on Jan. 22, 2004.

(30) Foreign Application Priority Data

Jan. 23, 2003    (FR) .................................. 03 00703

(51) Int. Cl.
*A61K 31/426* (2006.01)
(52) U.S. Cl. ...................... 514/370; 514/371
(58) Field of Classification Search .................. 514/370
See application file for complete search history.

(56) References Cited

U.S. PATENT DOCUMENTS 7,288,659 B2    10/2007    De Cointet et al.

FOREIGN PATENT DOCUMENTS

| WO | WO 98/22433 | 5/1998 |
|---|---|---|
| WO | WO 98/28268 | 7/1998 |
| WO | WO 00/24392 | 5/2000 |
| WO | WO 03/014095 | 2/2003 |

OTHER PUBLICATIONS

Pallàs et al., Current Pharmaceutical Design, (2006), 12(33), pp. 4389-4408.*
Kojima, et. al., Preparation of Amino Acid and .Alpha., .Beta.-Didehydroamino Acid Derivatives as .Beta.-Amyloid Formation Inhibitors, Database Ca 'Online! Chemical Abstracts Service, Columbus, Ohio, US; retrieved from STN Database accession No. 132:322142 abstract XP002193188, (2000).
Souillac, P., et. al., Characterization of Delivery Systems, Differential Scanning Calorimetry, In Encyclopedia of Controlled Drug Delivery, (1999) pp. 212-227 John Wiley & Sons.
Vippagunta, S. R., et al, Crystalline Solids, Advanced Drug Delivery Reviews; 48 (2001) pp. 3-26.

* cited by examiner

*Primary Examiner*—Laura L. Stockton
(74) *Attorney, Agent, or Firm*—Balaram Gupta

(57) ABSTRACT

The present invention discloses and claims therapeutic uses of a compound corresponding to the general formula (I):

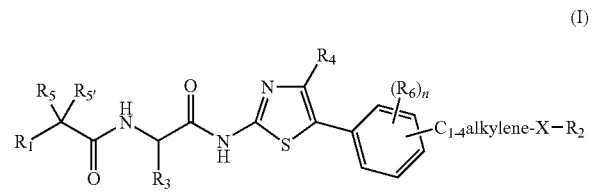

(I)

Wherein, X, $R_1$, $R_2$, $R_3$, $R_4$, $R_5$, $R_{5'}$, $R_6$ and n are as described herein.

3 Claims, No Drawings

THERAPEUTIC USE OF ACYLAMINOTHIAZOLE DERIVATIVES

CROSS-REFERENCE

This application is a divisional of U.S. application Ser. No. 11/186,507, filed Jul. 21, 2005, now U.S. Pat. No. 7,563,903, issued Jul. 21, 2009 which is a continuation of WO application no. PCT/FR2004/000140, filed 22 Jan., 2004, which claims the benefit of priority of French Application No. 03/00703, filed 23 Jan. 2003.

DESCRIPTION OF THE INVENTION

The subject of the invention is acylaminothiazole derivatives, their preparation and their therapeutic use.

SUMMARY OF THE INVENTION

The first subject of the invention is compounds corresponding to the general formula (I):

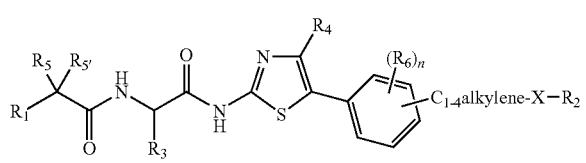

in which,

X represents an oxygen or sulfur atom;

$R_1$ represents a $C_{1-10}$ alkyl group optionally substituted with a $C_{3-7}$ cycloalkyl, a phenyl, a thienyl; or $R_1$ represents a $C_{3-7}$ cycloalkyl, thienyl, pyridinyl or pyrimidinyl group;

the thienyl groups being optionally substituted with one to 3 $C_{1-3}$ alkyl groups; the phenyl group being optionally substituted with one to 5 halogen atoms or $C_{1-3}$ alkyl, $C_{1-3}$ alkoxy, $C_{1-3}$ fluoroalkyl or $C_{1-3}$ fluoroalkoxy groups;

$R_2$ represents a $C_{1-6}$ alkyl group optionally substituted with a $C_{3-7}$ cycloalkyl, phenyl, $C_{1-3}$ alkoxy, hydroxyl group; or $R_2$ represents a $C_{3-7}$ cycloalkyl, piperidinyl, phenyl or pyridinyl group;

the $C_{3-7}$ cycloalkyl and piperidinyl groups being optionally substituted with one or more $C_{1-3}$ alkyl, $C_{1-3}$ alkoxy, hydroxyl, $C_{1-3}$ fluoroalkyl or $C_{1-3}$ fluoroalkoxy groups;

the phenyl and pyridinyl groups being optionally substituted with one or more halogen atoms or CN, $C_{1-3}$ alkyl, $C_{1-3}$ alkoxy, hydroxyl, $C_{1-3}$ fluoroalkyl or $C_{1-3}$ fluoroalkoxy groups;

$R_3$ represents a hydrogen atom or a $C_{1-6}$ alkyl group optionally substituted with a $C_{3-7}$ cycloalkyl group;

$R_4$ represents a hydrogen atom or a $C_{1-6}$ alkyl group;

$R_5$ and $R_{5'}$ represent, independently of each other, a hydrogen or halogen atom, a hydroxyl or $C_{1-3}$ alkyl group; or $R_5$ and $R_{5'}$ form together an oxo or oxime group such as:

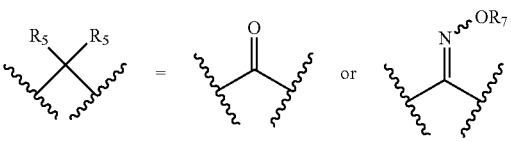

where $R_7$ represents a hydrogen atom or a $C_{1-3}$ alkyl; n represents an integer ranging from 0 to 3; and $R_6$ represents independently of each other when n=2 or 3, a hydrogen or halogen atom, a hydroxyl, $C_{1-3}$ alkyl, $C_{1-3}$ alkoxy, $C_{1-3}$ fluoroalkyl or $C_{1-3}$ fluoroalkoxy group.

DETAILED DESCRIPTION

Among the compounds of general formula (I), a sub-group of preferred compounds consists of the compounds for which:

X represents an oxygen or sulfur atom; and/or $R_1$ represents a $C_{1-5}$ alkyl group, preferably a methyl, ethyl, 1-methylethyl, 1,1-dimethylethyl, propyl, 1-methylpropyl, 2-methylpropyl, 1-ethylpropyl, optionally substituted with a phenyl, a thienyl; or $R_1$ represents a $C_{3-7}$ cycloalkyl group, preferably a cyclohexyl, a thienyl or pyridinyl group; the thienyl groups being optionally substituted with one or two $C_{1-3}$ alkyl groups, preferably a methyl; the phenyl group being optionally substituted with one or two halogen atoms, preferably chlorine or fluorine; and/or $R_2$ represents a $C_{1-6}$ alkyl group, preferably an ethyl, 1-methylethyl; or $R_2$ represents a $C_{3-7}$ cycloalkyl group, preferably a cyclohexyl, phenyl or pyridinyl;

the phenyl group being optionally substituted with one to three CN groups, $C_{1-3}$ alkyl groups, preferably methyl or ethyl, $C_{1-3}$ alkoxy groups, preferably methoxy, ethoxy or hydroxyl, fluoroalkoxy groups, preferably trifluoromethoxy, or halogen atoms, preferably chlorine or fluorine; and/or $R_3$ represents a $C_{1-6}$ alkyl group, preferably a methyl, ethyl or propyl group; and/or $R_4$ represents a hydrogen atom or a $C_{1-6}$ alkyl group, preferably a methyl or a 4-methylpentyl; and/or $R_5$ and $R_{5'}$ represent, independently of each other, a hydrogen atom or a hydroxyl; or $R_5$ and $R_{5'}$ form together an oxo group; and/or $R_6$ represents a hydrogen or halogen atom, preferably chlorine or fluorine, a $C_{1-3}$ alkyl, preferably a methyl, a $C_{1-3}$ alkoxy, preferably a methoxy or an ethoxy; and/or n is equal to 0 or 1.

The compounds for which X, $R_1$, $R_2$, $R_3$, $R_4$, $R_5$, $R_{5'}$, $R_6$ and n are all as defined above in the subgroup of preferred compounds are particularly preferred and more specifically among these the compounds for which:

X represents an oxygen atom; and/or the $C_{1-4}$ alkylene group is a methylene; and/or the carbon bearing the $R_3$ group is of (S) configuration.

By way of example of preferred compounds, the following compounds may be mentioned:

1. (2S)-2-{[(2R)-2-cyclohexyl-2-hydroxyacetyl]amino}-N-(5-{2-[(cyclohexyloxy)methyl]phenyl}-1,3-thiazol-2-yl)pentanamide 2. (2S)-2-{[(2S)-2-cyclohexyl-2-hydroxyacetyl]amino}-N-(5-{2-[(cyclohexyloxy)methyl]phenyl}-1,3-thiazol-2-yl)pentanamide
3. (2S)—N-(5-{2-[(cyclohexyloxy)methyl]phenyl}-1,3-thiazol-2-yl)-2-{[2-(3-pyridinyl)acetyl]amino}pentanamide
4. N-((1S)-1-{[(5-{2-[(cyclohexyloxy)methyl]phenyl}-1,3-thiazol-2-yl)amino]carbonyl}butyl)-2-hydroxy-4-methylpentanamide
5. (2S)—N-{5-[2-(isopropoxymethyl)phenyl]-4-methyl-1,3-thiazol-2-yl}-2-{[2-(3-thienyl)acetyl]amino}pentanamide
6. (2S)—N-{5-[2-(isopropoxymethyl)phenyl]-1,3-thiazol-2-yl}-2-{[2-(3-thienyl)acetyl]amino}pentanamide
7. (2S)—N-{5-[2-(isopropoxymethyl)phenyl]-1,3-thiazol-2-yl}-2-{[3-(3-thienyl)propanoyl]amino}pentanamide
8. (2S)—N-{5-[2-(phenoxymethyl)phenyl]-1,3-thiazol-2-yl}-2-{[2-(3-thienyl)acetyl]amino}pentanamide
9. (2S)-2-{[(2S)-2-hydroxy-3,3-dimethylbutanoyl]amino}-N-{5-[2-(phenoxymethyl)phenyl]-1,3-thiazol-2-yl}pentanamide
10. (2S)—N-{5-[2-(phenoxymethyl)phenyl]-1,3-thiazol-2-yl}-2-{[2-(2-thienyl)acetyl]amino}butanamide
11. (2S)-2-{[(2S)-2-hydroxy-3,3-dimethylbutanoyl]amino}-N-{5-[2-(isopropoxymethyl)phenyl]-1,3-thiazol-2-yl}pentanamide
12. (2S)—N-{5-[2-(isopropoxymethyl)phenyl]-1,3-thiazol-2-yl}-2-{[2-(2-thienyl)acetyl]amino}pentanamide
13. (2S)-2-[(3,3-dimethylbutanoyl)amino]-N-{5-[2-(isopropoxymethyl)phenyl]-1,3-thiazol-2-yl}pentanamide
14. N-{(1S)-1-[({5-[2-(isopropoxymethyl)phenyl]-1,3-thiazol-2-yl}amino)carbonyl]butyl}-3-methyl-2-oxopentanamide
15. (2S)—N-{5-[2-(ethoxymethyl)phenyl]-1,3-thiazol-2-yl}-2-{[(2S)-2-hydroxy-3,3-dimethylbutanoyl]amino}pentanamide
16. (2S)-2-{[2-(2,5-dimethyl-3-thienyl)acetyl]amino}-N-{5-[2-(ethoxymethyl)phenyl]-1,3-thiazol-2-yl}pentanamide
17. (2S)-2-{[(2S)-2-hydroxy-3,3-dimethylbutanoyl]amino}-N-[5-(2-{[3-(trifluoromethoxy)phenoxy]methyl}phenyl)-1,3-thiazol-2-yl]pentanamide
18. (2S)-2-{[(2S)-2-hydroxy-3,3-dimethylbutanoyl]amino}-N-{5-[4-methoxy-2-(phenoxymethyl)phenyl]-1,3-thiazol-2-yl}pentanamide
19. (2S)—N-(5-{2-[(2-fluorophenoxy)methyl]phenyl}-1,3-thiazol-2-yl)-2-{[(2S)-2-hydroxy-3,3-dimethylbutanoyl]amino}pentanamide
20. (2S)—N-(5-{2-[(2-ethylphenoxy)methyl]phenyl}-1,3-thiazol-2-yl)-2-{[(2S)-2-hydroxy-3,3-dimethylbutanoyl]amino}pentanamide
21. (2S)-2-{[3-(2,4-dichlorophenyl)propanoyl]amino}-N-{5-[2-(phenoxymethyl)phenyl]-1,3-thiazol-2-yl}pentanamide
22. (2S)-2-{[2-(5-methyl-2-thienyl)acetyl]amino}-N-{5-[2-(phenoxymethyl)phenyl]-1,3-thiazol-2-yl}pentanamide
23. (2S)—N-(5-{2-[(2,3-dimethoxyphenoxy)methyl]-phenyl}-1,3-thiazol-2-yl)-2-{[(2S)-2-hydroxy-3,3-dimethylbutanoyl]amino}pentanamide
24. (2S)-2-{[(2S)-2-hydroxy-3,3-dimethylbutanoyl]amino}-N-[5-(2-{[2-(trifluoromethoxy)phenoxy]methyl}phenyl)-1,3-thiazol-2-yl]pentanamide
25. (2S)—N-(5-{2-[(3,5-dimethoxyphenoxy)methyl]-phenyl}-1,3-thiazol-2-yl)-2-{[(2S)-2-hydroxy-3,3-dimethylbutanoyl]amino}pentanamide
26. (2S)—N-(5-{2-[(2,3-dimethylphenoxy)methyl]phenyl}-1,3-thiazol-2-yl)-2-{[(2S)-2-hydroxy-3,3-dimethylbutanoyl]amino}pentanamide
27. (2S)—N-(5-{2-[(3,4-dimethylphenoxy)methyl]phenyl}-1,3-thiazol-2-yl)-2-{[(2S)-2-hydroxy-3,3-dimethylbutanoyl]amino}pentanamide
28. (2S)—N-(5-{2-[(2,6-dimethylphenoxy)methyl]phenyl}-1,3-thiazol-2-yl)-2-{[(2S)-2-hydroxy-3,3-dimethylbutanoyl]amino}pentanamide
29. (2S)—N-(5-{2-[(3-chlorophenoxy)methyl]phenyl}-1,3-thiazol-2-yl)-2-{[(2S)-2-hydroxy-3,3-dimethylbutanoyl]amino}pentanamide
30. (2S)—N-(5-{2-[(3,4-dimethoxyphenoxy)methyl]phenyl}-1,3-thiazol-2-yl)-2-{[(2S)-2-hydroxy-3,3-dimethylbutanoyl]amino}pentanamide
31. (2S)—N-(5-{2-[(2,6-dimethoxyphenoxy)methyl]phenyl}-1,3-thiazol-2-yl)-2-{[(2S)-2-hydroxy-3,3-dimethylbutanoyl]amino}pentanamide
32. (2S)—N-(5-{2-[(2,4-dimethylphenoxy)methyl]phenyl}-1,3-thiazol-2-yl)-2-{[(2S)-2-hydroxy-3,3-dimethylbutanoyl]amino}pentanamide
33. (2S)—N-(5-{2-[(2,5-dimethylphenoxy)methyl]phenyl}-1,3-thiazol-2-yl)-2-{[(2S)-2-hydroxy-3,3-dimethylbutanoyl]amino}pentanamide
34. (2S)-2-{[(2S)-2-hydroxy-3,3-dimethylbutanoyl]amino}-N-{4-methyl-5-[2-(phenoxymethyl)phenyl]-1,3-thiazol-2-yl}pentanamide
35. (2R)-2-{[(2S)-2-hydroxy-3,3-dimethylbutanoyl]amino}-N-{5-[2-(phenoxymethyl)phenyl]-1,3-thiazol-2-yl}pentanamide
36. (2S)-2-{[(2S)-2-hydroxy-3,3-dimethylbutanoyl]amino}-N-(5-{2-[(2-methylphenoxy)methyl]phenyl}-1,3-thiazol-2-yl)pentanamide
37. (2S)-2-{[(2S)-2-hydroxy-3-methylbutanoyl]amino}-N-{5-[2-(phenoxymethyl)phenyl]-1,3-thiazol-2-yl}pentanamide
38. (2S)-2-[(2-hydroxy-3,3-dimethylbutanoyl)amino]-N-(5-{2-[(2-methoxyphenoxy)methyl]phenyl}-1,3-thiazol-2-yl)pentanamide
39. (2S)—N-(5-{2-[(2-ethoxyphenoxy)methyl]phenyl}-1,3-thiazol-2-yl)-2-[(2-hydroxy-3,3-dimethylbutanoyl)amino]pentanamide
40. (2S)-2-[(2-hydroxy-3-phenylpropanoyl)amino]-N-{5-[2-(phenoxymethyl)phenyl]-1,3-thiazol-2-yl}pentanamide
41. (2S)—N-(5-{2-[(2,6-dichlorophenoxy)methyl]phenyl}-1,3-thiazol-2-yl)-2-[(2-hydroxy-3,3-dimethylbutanoyl)amino]pentanamide
42. (2R)-3-ethyl-2-hydroxy-N-{(1S)-1-[({5-[2-(phenoxymethyl)phenyl]-1,3-thiazol-2-yl}amino)carbonyl]butyl}pentanamide
43. (2S)-3-ethyl-2-hydroxy-N-{(1S)-1-[({5-[2-(phenoxymethyl)phenyl]-1,3-thiazol-2-yl}amino)carbonyl]butyl}pentanamide
44. (2S)-2-{[(2S)-2-hydroxy-3,3-dimethylbutanoyl]amino}-N-{5-[2-(isopropoxymethyl)-4-methoxyphenyl]-1,3-thiazol-2-yl}pentanamide
45. (2S)—N-(5-{2-[(2-(chloro-6-methylphenoxy)methyl]phenyl}-1,3-thiazol-2-yl)-2-{[(2S)-2-hydroxy-3,3-dimethylbutanoyl]amino}pentanamide
46. (2S)—N-(5-{2-[(2,6-difluorophenoxy)methyl]phenyl}-1,3-thiazol-2-yl)-2-{[(2S)-2-hydroxy-3,3-dimethylbutanoyl]amino}pentanamide
47. (2S)—N-{5-[4-chloro-2-(phenoxymethyl)phenyl]-1,3-thiazol-2-yl}-2-{[(2S)-2-hydroxy-3,3-dimethylbutanoyl]amino}pentanamide
48. (2S)—N-{5-[4-fluoro-2-(phenoxymethyl)phenyl]-1,3-thiazol-2-yl}-2-{[(2S)-2-hydroxy-3,3-dimethylbutanoyl]amino}pentanamide 49. (2S)-2-{[(2S)-2-hydroxy-3-methylbutanoyl]amino}-N-{5-[4-methoxy-2-(phenoxymethyl)phenyl]-1,3-thiazol-2-yl}pentanamide
50. (2S)—N-(5-{2-[(3,4-dichlorophenoxy)methyl]phenyl}-1,3-thiazol-2-yl)-2-{[(2S)-2-hydroxy-3,3-dimethylbutanoyl]amino}pentanamide
51. (2S)—N-((1S)-1-{[(5-{2-[(cyclohexyloxy)methyl]phenyl}-1,3-thiazol-2-yl)amino]carbonyl}butyl)-2-hydroxy-4-methylpentanamide
52. (2S)—N-{5-[4-ethoxy-2-(phenoxymethyl)phenyl]-1,3-thiazol-2-yl}-2-{[(2S)-2-hydroxy-3,3-dimethylbutanoyl]amino}pentanamide
53. (2S)—N-{5-[4-ethoxy-2-(phenoxymethyl)phenyl]-1,3-thiazol-2-yl}-2-{[(2S)-2-hydroxy-3-methylbutanoyl]amino}pentanamide
54. (2S)—N-{5-[5-fluoro-2-(phenoxymethyl)phenyl]-1,3-thiazol-2-yl}-2-{[(2S)-2-hydroxy-3,3-dimethylbutanoyl]amino}pentanamide
55. (2S)—N-{5-[5-chloro-2-(phenoxymethyl)phenyl]-1,3-thiazol-2-yl}-2-{[(2S)-2-hydroxy-3,3-dimethylbutanoyl]amino}pentanamide
56. (2S)—N-{5-[5-fluoro-2-(phenoxymethyl)phenyl]-1,3-thiazol-2-yl}-2-{[(2S)-2-hydroxy-3-methylbutanoyl]amino}pentanamide
57. (2S)—N-(5-{2-[(cyclohexyloxy)methyl]phenyl}-1,3-thiazol-2-yl)-2-{[(2S)-2-hydroxy-3,3-dimethylbutanoyl]amino}pentanamide
58. (2S)-2-hydroxy-3,3-dimethyl-N-[(1S)-1-methyl-2-oxo-2-({5-[2-(phenoxymethyl)phenyl]-1,3-thiazol-2-yl}amino)ethyl]butanamide
59. (2S)-2-{[(2S)-2-hydroxy-3,3-dimethylbutanoyl]amino}-N-{5-[4-methyl-2-(phenoxymethyl)phenyl]-1,3-thiazol-2-yl}pentanamide
60. (2S)-2-{[(2S)-2-hydroxy-3-methylbutanoyl]amino}-N-{5-[5-methyl-2-(phenoxymethyl)phenyl]-1,3-thiazol-2-yl}pentanamide
61. (2S)—N-(5-{2-[(3-cyanophenoxy)methyl]phenyl}-1,3-thiazol-2-yl)-2-{[(2S)-2-hydroxy-3,3-dimethylbutanoyl]amino}pentanamide
62. (2S)—N-(5-{2-[(3-fluorophenoxy)methyl]phenyl}-1,3-thiazol-2-yl)-2-{[(2S)-2-hydroxy-3,3-dimethylbutanoyl]amino}pentanamide
63. (2S)—N-(5-{2-[(3-fluorophenoxy)methyl]phenyl}-1,3-thiazol-2-yl)-2-{[(2S)-2-hydroxy-3-methylbutanoyl]amino}pentanamide
64. (2S)-2-{[(2S)-2-hydroxy-3,3-dimethylbutanoyl]amino}-N-{5-[5-methyl-2-(phenoxymethyl)phenyl]-1,3-thiazol-2-yl}pentanamide
65. (2S)-2-{[(2S)-2-hydroxy-3-methylbutanoyl]amino}-N-{5-[4-methyl-2-(phenoxymethyl)phenyl]-1,3-thiazol-2-yl}pentanamide
66. (2S)—N-{(1S)-2-[(5-{2-[(cyclohexyloxy)methyl]phenyl}-1,3-thiazol-2-yl)amino]-1-methyl-2-oxoethyl}-2-hydroxy-3,3-dimethylbutanamide
67. (2S)—N-(5-{2-[(2-chloro-5-methylphenoxy)methyl]phenyl}-1,3-thiazol-2-yl)-2-{[(2S)-2-hydroxy-3,3-dimethylbutanoyl]amino}pentanamide
68. (2S)-2-{[(2S)-2-hydroxy-3,3-dimethylbutanoyl]amino}-N-(5-{2-[(3-methylphenoxy)methyl]phenyl}-1,3-thiazol-2-yl)pentanamide
69. (2S)—N-(5-{2-[(2-cyanophenoxy)methyl]phenyl}-1,3-thiazol-2-yl)-2-{[(2S)-2-hydroxy-3,3-dimethylbutanoyl]amino}pentanamide
70. (2S)-2-{[(2S)-2-hydroxy-3,3-dimethylbutanoyl]amino}-N-(5-{2-[(4-pyridinyloxy)methyl]phenyl}-1,3-thiazol-2-yl)pentanamide
71. (2S)—N-(5-{2-[(2-chloro-4,5-dimethylphenoxy)methyl]phenyl}-1,3-thiazol-2-yl)-2-{[(2S)-2-hydroxy-3,3-dimethylbutanoyl]amino}pentanamide
72. (2S)—N-(5-{2-[(4-chloro-3-methylphenoxy)methyl]phenyl}-1,3-thiazol-2-yl)-2-{[(2S)-2-hydroxy-3,3-dimethylbutanoyl]amino}pentanamide
73. (2S)—N-(5-{2-[(2,3-dichlorophenoxy)methyl]phenyl}-1,3-thiazol-2-yl)-2-{[(2S)-2-hydroxy-3,3-dimethylbutanoyl]amino}pentanamide
74. (2S)—N-(5-{2-[(2,3-difluorophenoxy)methyl]phenyl}-1,3-thiazol-2-yl)-2-{[(2S)-2-hydroxy-3,3-dimethylbutanoyl]amino}pentanamide
75. (2S)-2-{[(2S)-2-hydroxy-3,3-dimethylbutanoyl]amino}-N-{4-(4-methylpentyl)-5-[2-(phenoxymethyl)phenyl]-1,3-thiazol-2-yl}pentanamide The subject of the invention is also, among the compounds of general formula (I), compounds corresponding to general formula (I'):

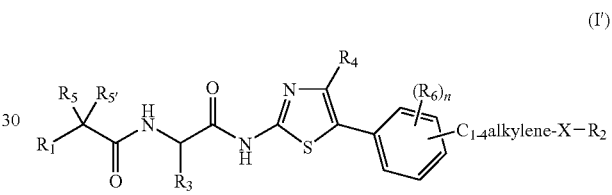

(I')

in which,

X represents an oxygen or sulfur atom;

$R_1$ represents a $C_{1-10}$ alkyl group optionally substituted with a $C_{3-7}$ cycloalkyl, a phenyl or a thienyl; or $R_1$ represents a $C_{3-7}$ cycloalkyl, thienyl, pyridinyl or pyrimidinyl group;

the thienyl groups being optionally substituted with one to 3 $C_{1-3}$ alkyl groups; the phenyl group being optionally substituted with one to 5 halogen atoms or $C_{1-3}$ alkyl, $C_{1-3}$ alkoxy, $C_{1-3}$ fluoroalkyl or $C_{1-3}$ fluoroalkoxy groups;

$R_2$ represents a $C_{1-6}$ alkyl group optionally substituted with a $C_{3-7}$ cycloalkyl, phenyl, $C_{1-3}$ alkoxy or hydroxyl group; or $R_2$ represents a $C_{3-7}$ cycloalkyl, piperidinyl, phenyl or pyridinyl group;

the $C_{3-7}$ cycloalkyl and piperidinyl groups being optionally substituted with one or more $C_{1-3}$ alkyl, $C_{1-3}$ alkoxy, hydroxyl, $C_{1-3}$ fluoroalkyl or $C_{1-3}$ fluoroalkoxy groups;

the phenyl and pyridinyl groups being optionally substituted with one or more halogen atoms or $C_{1-3}$ alkyl, $C_{1-3}$ alkoxy, hydroxyl, $C_{1-3}$ fluoroalkyl or $C_{1-3}$ fluoroalkoxy groups;

$R_3$ represents a hydrogen atom or a $C_{1-6}$ alkyl group optionally substituted with a $C_{3-7}$ cycloalkyl group;

$R_4$ represents a hydrogen atom or a $C_{1-4}$ alkyl group;

$R_5$ and $R_{5'}$ represent, independently of each other, a hydrogen or halogen atom, a hydroxyl or $C_{1-3}$ alkyl group; or $R_5$ and $R_{5'}$ form together an oxo or oxime group such as:

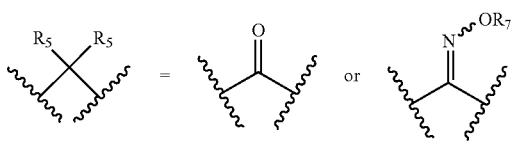

where $R_7$ represents a hydrogen atom or a $C_{1-3}$ alkyl;

n represents an integer ranging from 0 to 3; and $R_6$ represents independently of each other when n=2 or 3, a hydrogen or halogen atom, a hydroxyl, $C_{1-3}$ alkyl, $C_{1-3}$ alkoxy, $C_{1-3}$ fluoroalkyl or $C_{1-3}$ fluoroalkoxy group.

Among the compounds of general formula (I'), a sub-group of preferred compounds consists of the compounds for which:

X represents an oxygen or sulfur atom; and/or $R_1$ represents a $C_{1-5}$ alkyl group, preferably a methyl, ethyl, 1-methylethyl, 1,1-dimethylethyl, propyl, 1-methylpropyl, 2-methylpropyl, 1-ethylpropyl, optionally substituted with a phenyl, a thienyl; or $R_1$ represents a $C_{3-7}$ cycloalkyl group, preferably a cyclohexyl, a thienyl or pyridinyl group; the thienyl groups being optionally substituted with one or two $C_{1-3}$ alkyl groups, preferably a methyl; the phenyl group being optionally substituted with one or two halogen atoms, preferably chlorine or fluorine; and/or $R_2$ represents a $C_{1-6}$ alkyl group, preferably an ethyl, 1-methylethyl; or $R_2$ represents a $C_{3-7}$ cycloalkyl group, preferably a cyclohexyl or phenyl;

the phenyl group being optionally substituted with 1 or 2 $C_{1-3}$ alkyl groups, preferably methyl or ethyl, $C_{1-3}$ alkoxy groups, preferably methoxy, ethoxy or hydroxyl, fluoroalkoxy groups, preferably trifluoromethoxy, or with one or two halogen atoms, preferably chlorine or fluorine; and/or $R_3$ represents a $C_{1-6}$ alkyl group, preferably an ethyl or propyl; and/or $R_4$ represents a hydrogen atom or a $C_{1-4}$ alkyl group, preferably a methyl; and/or $R_5$ and $R_{5'}$ represent, independently of each other, a hydrogen atom or a hydroxyl; or $R_5$ and $R_{5'}$ form together an oxo group; and/or $R_6$ represents a hydrogen or halogen atom, preferably a chlorine or a fluorine, a $C_{1-3}$ alkoxy, preferably a methoxy; and/or n is equal to 0 or 1

In the context of the invention, the expression:

$C_{t-z}$ where t and z may take the values from 1 to 10, is understood to mean a carbon chain which may have from t to z carbon atoms, for example $C_{1-3}$ a carbon chain which may have from 1 to 3 carbon atoms, $C_{3-6}$ a carbon chain which may have from 3 to 6 carbon atoms; and the like;

alkyl is understood to mean a linear or branched saturated aliphatic group, for example a $C_{1-6}$ alkyl group represents a linear or branched carbon chain of from 1 to 6 carbon atoms, more particularly a methyl, ethyl, propyl, 1-methylethyl, butyl, 1-methylpropyl, 2-methylpropyl, 1,1-dimethylethyl, and the like, preferably a methyl, ethyl, propyl or 1-methylethyl;

alkylene is understood to mean a divalent alkyl group;

cycloalkyl is understood to mean a cyclic alkyl group, for example a $C_{3-7}$ cycloalkyl group represents a carbon cycle of from 3 to 7 carbon atoms, more particularly a cyclopropyl, cyclobutyl, cyclopentyl, cyclohexyl, cycloheptyl, preferably a cyclopentyl or cyclohexyl;

alkoxy is understood to mean an —O-alkyl group where the alkyl group is as defined above;

fluoroalkyl is understood to mean an alkyl group in which one or more hydrogen atoms have been substituted with a fluorine atom;

fluoroalkoxy is understood to mean an alkoxy group in which one or more hydrogen atoms have been substituted with a fluorine atom; and halogen atom is understood to mean a fluorine, a chlorine, a bromine or an iodine.

The compounds of general formula (I) may contain one or more asymmetric carbons. They may therefore exist in the form of enantiomers or of diastereoisomers. These enantiomers or diastereoisomers, and mixtures thereof, including the racemic mixtures, form part of the invention.

The compounds of formula (I) may exist in the form of bases or of addition salts with acids. Such addition salts form part of the invention.

These salts are advantageously prepared with pharmaceutically acceptable acids, but the salts of other useful acids, for example, for the purification or the isolation of the compounds of formula (I), also form part of the invention.

The compounds of general formula (I) may exist in the form of hydrates or of solvates, namely in the form of associations or combinations with one or more molecules of water or with a solvent. Such hydrates and solvates also form part of the invention.

In the text which follows, the expression leaving group is understood to mean a group which can be easily cleaved from a molecule, with departure of an electron pair, by the breaking of a heterolytic bond. This group may thus be easily replaced by another group during a substitution reaction for example. Such leaving groups are, for example, halogens, or an activated hydroxyl group such as a mesylate, tosylate, triflate, acetyl and the like. Examples of leaving groups and references for their preparation are given in "Advanced Organic Chemistry", J. March, 3$^{rd}$ Edition, Wiley Interscience, p. 310-316.

The expression protecting group is understood to mean a group which makes it possible to prevent the reactivity of a functional group or a position, during a chemical reaction which may effect it, and which releases the molecule after cleavage according to methods known to persons skilled in the art. Examples of protecting groups and methods of protection and deprotection are given, inter alia, in *Protective groups in Organic Synthesis*, Greene et al., 2$^{nd}$ Ed. (John Wiley & Sons, Inc., New York).

The second subject of the invention is methods for preparing the compounds of formula (I).

Thus, these compounds may be prepared by methods, illustrated in the schemes which follow, whose operating conditions are conventional for persons skilled in the art.

Scheme 1

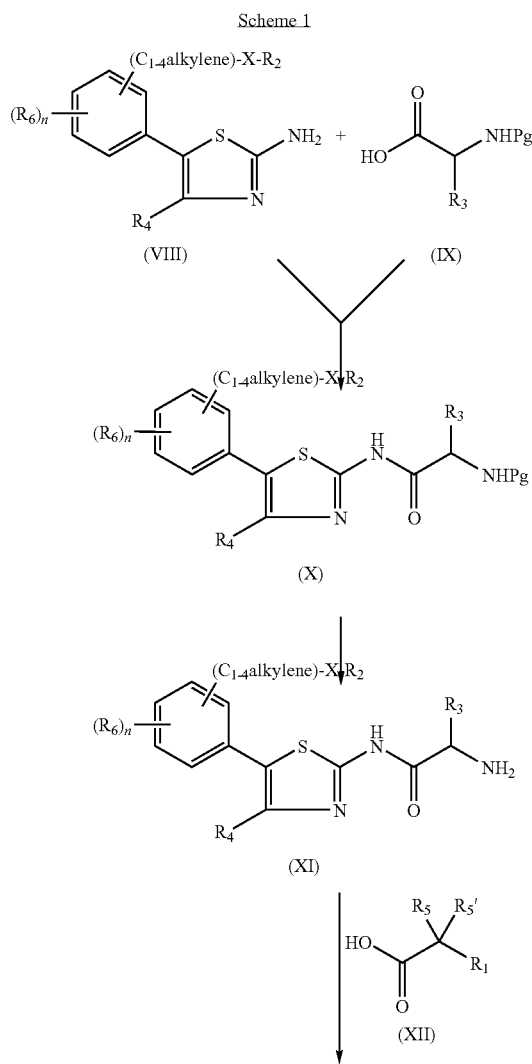

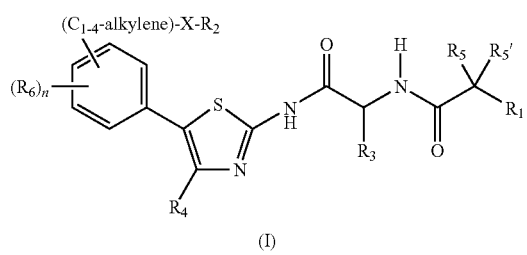

According to Scheme 1, the compound of formula (I) may be obtained by peptide coupling of the amine of formula (XI) with the acid of formula (XII) according to conditions known to persons skilled in the art, for example in the presence of benzotriazol-1-yloxy-tris(dimethylamino)phosphonium hexafluoro-phosphate (BOP) and N-ethylmorpholine or N-methylmorpholine in an inert solvent such as dimethylformamide, acetonitrile or dichloromethane at a temperature which may range from 0° C. to room temperature.

The amine of formula (XI) is obtained by peptide coupling of the amine of formula (VIII) with the amino acid of formula (IX), in which Pg represents a protecting group, under conditions as described above, to give the compound of formula (X). The amino acid of formula (IX) is, for example, protected by means of an N-tert-butyloxycarbonyl (Boc). The compound (X) is then deprotected according to methods known to persons skilled in the art, to give the amine of formula (XI). For example, if the protecting group used is Boc, the latter may be deprotected by acid hydrolysis, in the presence of anhydrous gaseous hydrochloric acid.

The compound of formula (VIII) may be prepared according to Scheme 2.

Scheme 2

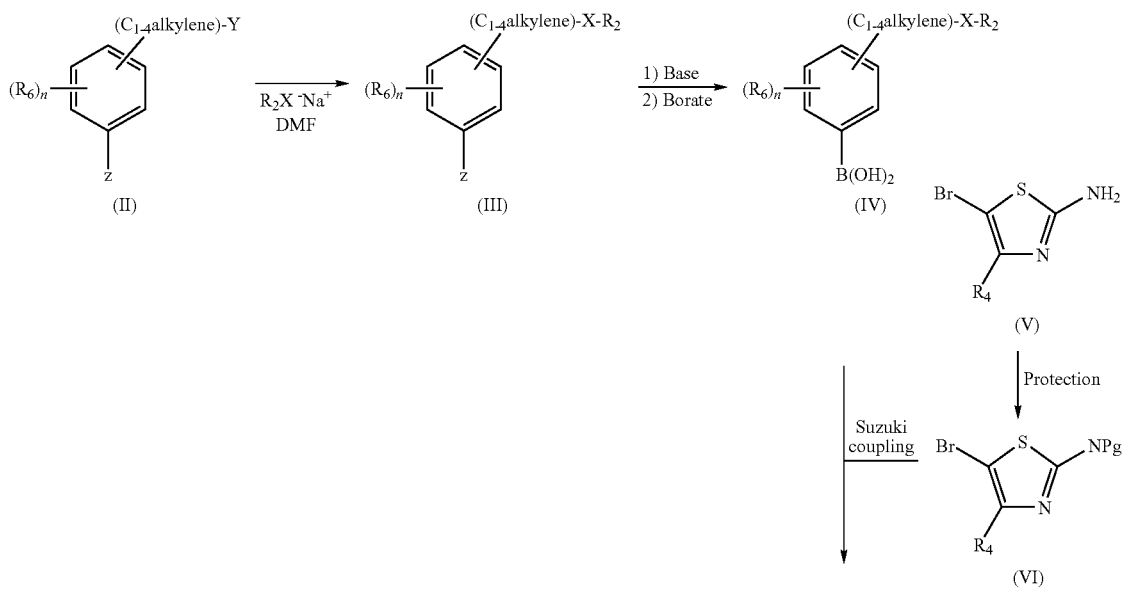

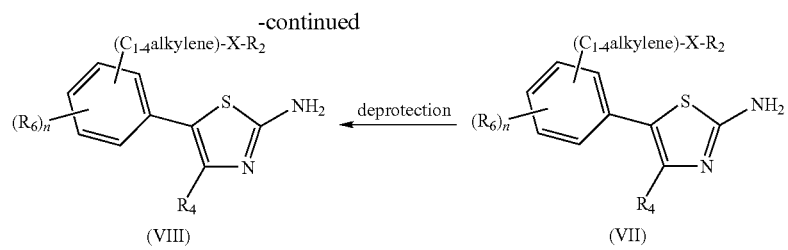

According to this scheme, the aralkyl of formula (II), in which Y represents a leaving group, preferably a halogen atom such as bromine and Z represents a halogen atom such as bromine, is condensed with an alkali metal thiolate or alcoholate, for example of formula $R_2X^-Na^+$ in which X represents an oxygen or sulfur atom. The reaction is carried out in an inert solvent such as dimethylformamide at a temperature which may range from 0° C. to 50° C., to give the compound of formula (III). The aryl or formula (III) is converted to boronic acid of formula (IV) according to an adaptation of the method described by Schoevaars, J. Am. Chem. Soc., 1999, 121, 9550-9561. The conversion may, for example, be carried out by prior formation of the anion of the compound of formula (III), for example by the action of a strong base such as butyllithium, in an ethereal solvent such as tetrahydrofuran, at temperatures which may range from −50° C. to −80° C. This anion is then reacted with a borate such as trimethyl borate to give, after hydrolysis, the boronic acid of formula (IV).

The coupling of the boronic acid (IV) with the 5-bromothiazole of formula (VI) in which Pg represents a protecting group, such as an imino, for example a diphenyl ketone imine, may be carried out according to the Suzuki reaction, by adaptation of the method described by Wolfe, J. Org. Chem., 1997, 62, 4943-4948, to give the 5-phenylthiazole of formula (VII). The coupling is carried out, for example, in an ethereal solvent such as dioxane in the presence of tripotassium phosphate trihydrate and a catalyst such as tetrakis(triphenylphosphine)palladium (0) at a temperature which may range from room temperature to the reflux temperature of the solvent. The 5-phenylthiazole of formula (VII) thus prepared is then deprotected according to methods known to persons skilled in the art to generate the 5-phenyl-2-aminothiazole of formula (VIII).

The 5-bromothiazole of formula (VI) is obtained by protecting the amino functional group of the corresponding compound of formula (V). Preferably, it is protected in the form of a diphenyl ketone imine under conditions known to persons skilled in the art.

The starting compounds, in particular the compounds of formula (II), (V), (IX) and (XII) are commercially available or are described in the literature, or may be prepared by methods which are described therein or which are known to persons skilled in the art.

For example, 5-bromo-2-aminothiazole (V) may be obtained by bromination of the corresponding 2-aminothiazole according to an adaptation of the method described by Kaye, J. Chem. Soc. Perkin I, 1981, 2335-2339.

For example, the compound of formula (XII) may be obtained by adaptation of the methods described by Middleton et al., J. Org. Chem., 45, 14, 1980, 2883-2887 and by Miyamoto et al., J. Amer. Chem. Soc., 114, 15, 1992, 6256-6257.

The meanings of X, $R_1$, $R_2$, $R_3$, $R_4$, $R_5$, $R_{5'}$, $R_6$ and n in the compounds of formula (II) to (XII) are as defined for the compounds of formula (I).

The following examples describe the preparation of some compounds in accordance with the invention. These examples are not limiting and only illustrate the invention. The exemplified compound numbers refer to those given in the Table below. The elemental microanalyses and the NMR, IR or mass spectra confirm the structure of the compounds obtained.

Example 1

Compound No. 9

(2S)-2-{[(2S)-2-hydroxy-3,3-dimethylbutanoyl]amino}-N-{5-[2-(phenoxymethyl)phenyl]-1,3-thiazol-2-yl}pentanamide 1.1 1-bromo-2-(phenoxymethyl)benzene 1.2 g of sodium hydride (at 50% in suspension in oil) are added at 5° C., in portions, to 20.2 g of phenol in solution in 150 ml of dimethylformamide.

The mixture is stirred at room temperature and 37.2 g of 2-bromobenzyl bromide in solution in 15 ml of dimethylformamide are introduced at 5° C. After 2 hours at 20° C., the reaction medium is poured over ice-cold water and extracted with ethyl acetate. The organic phase is dried over anhydrous sodium sulfate and concentrated to give 36 g of oil.

$^1$H NMR: δ in ppm (DMSO $d_6$): 5.22 (s, 2H); 7.09-7.67 (unresolved complex, 9H).

1.2 2-(phenoxymethyl)phenylboronic acid 90 ml of n-butyllithium (1.6 M) in solution in hexane are added dropwise at −70° C. to 36 g of 1-bromo-2-(phenoxymethyl)benzene, obtained in step 1.1, in solution in 150 ml of tetrahydrofuran. After 2 hours at −70° C., 16 ml of trimethyl borate are introduced dropwise. The temperature of the reaction medium is allowed to rise to −30° C. The medium is hydrolyzed with a saturated ammonium chloride solution, and then extracted with ethyl acetate and the organic phase is dried with anhydrous sodium sulfate. After evaporation, 33 g of a white solid are obtained.

$^1$H NMR: δ in ppm (DMSO $d_6$): 5.25 (s, 2H); 6.85-7.67 (unresolved complex, 11H).

1.3 5-bromo-N-(diphenylmethylene)-1,3-thiazol-2-amine 26 g of benzophenone imine are added to 34 g of 5-bromo-1,3-thiazol-2-amine hydrobromide, in suspension in 300 ml of 1,2-dichloroethane. The mixture is kept under reflux for 18 hours. The precipitate formed is filtered and the filtrate is concentrated to give 37.2 g of solid.

m.p.=109° C.

$^1$H NMR: δ in ppm (DMSO d$_6$): 7.34 (m, 2H); 7.50-7.76 (unresolved complex, 9H).

1.4 5-{2-[(phenoxy)methyl]phenyl}-N-(diphenylmethylene)-1,3-thiazol-2-amine 15 g of tripotassium phosphate dihydrate, 10.5 g of 5-bromo-N-(diphenylmethylene)-1,3-thiazol-2-amine, obtained in step 1.3, and 1.5 g of tetrakis(triphenylphosphine) palladium(0) are successively introduced into 14.8 g of 2-(phenoxymethyl)phenylboronic acid, obtained in step 1.2, in solution in 250 ml of 1,4-dioxane, and the mixture is kept under reflux for 1 hour. The reaction medium is evaporated to dryness, the residue is taken up in ethyl acetate and washed with water. The organic phase is dried over anhydrous sodium sulfate and the solvates are concentrated. The residue is chromatographed on a silica gel column, eluting with dichloromethane to give 35 g of a yellow oil.

$^1$H NMR: δ in ppm: 4.81 (s, 2H); 7.17-7.83 (unresolved complex, 20H).

1.5 5-{2-[(phenoxy)methyl]phenyl}-1,3-thiazol-2-amine 150 ml of an aqueous hydrochloric acid solution (1 M) are added to 35 g of 5-{2-[(phenoxy)methyl]phenyl}-N-(diphenylmethylene)-1,3-thiazol-2-amine, obtained in step 1.4, in solution in 250 ml of methanol, and the mixture is stirred for 18 hours at 20° C. The mixture is evaporated to dryness, the residue is taken up in diethyl ether and washed with an aqueous sodium hydroxide solution (0.5 M). The organic phase is dried over anhydrous sodium sulfate and concentrated. The residue is chromatographed on a silica gel column, eluting with a dichloromethane/methanol 98/2 (v/v) mixture, to give 15 g of a beige solid.

m.p.=154° C.

$^1$H NMR: δ in ppm (DMSO d$_6$): 5.07 (s, 2H); 6.98-7.65 (unresolved complex, 10H).

1.6 tert-butyl (1S)-1-[({5-[2-(phenoxymethyl)phenyl]-1,3-thiazol-2-yl}amino)carbonyl]butylcarbamate 7.1 g of benzotriazol-1-yloxytris(dimethylamino)phosphonium hexafluorophosphate are added at 0° C. to 3.35 g of (2S)-2-[(tert-butyloxycarbonyl)amino]pentanoic acid in solution in 35 ml of dimethylformamide, followed dropwise by 2.1 ml of N-methylmorpholine. After 15 minutes at 0° C., 4 g of 5-{2-[(phenoxy)methyl]phenyl}-1,3-thiazol-2-amine, obtained in step 1.5, are introduced and the mixture is stirred for 18 hours at room temperature. The medium is taken up in ethyl acetate and washed twice with water. The organic phase is dried over anhydrous sodium sulfate and concentrated. The residue is chromatographed on a silica gel column, eluting with a dichloromethane/methanol 98/2 (v/v) mixture to give 5.2 g of a colorless oil.

$^1$H NMR: δ in ppm (DMSO d$_6$): 0.88 (t, 3H); 1.22-1.65 (unresolved complex, 13H); 4.24 (q, 1H); 5.09 (s, 2H); 6.94-7.67 (unresolved complex, 10H); 12.23 (s, 1H).

1.7 (2S)-2-amino-N-(5-{2-[(phenoxy)methyl]phenyl}-1,3-thiazol-2-yl)pentanamide hydrochloride 25 ml of a solution of gaseous hydrochloric acid (4.5 M) in ethyl acetate are added dropwise at 0° C. to 5 g of tert-butyl (1S)-2-[(5-{2-[(phenoxy)-methyl]phenyl}-1,3-thiazol-2-yl)amino]-1-propyl-2-oxoethylcarbamate, obtained in step 1.6, in solution in 60 ml of ethyl acetate. The mixture is stirred for 18 hours at 20° C. The precipitate formed is filtered, rinsed twice with diethyl ether and dried to give 3 g of a white solid.

m.p.=148° C.

$^1$H NMR: δ in ppm (DMSO d$_6$): 0.90 (t, 3H); 1.39 (m, 2H); 1.85 (m, 2H); 4.18 (q, 1H); 5.08 (s, 2H); 6.94-7.68 (unresolved complex, 10H); 8.65 (s, 3H).

1.8 (2S)-2-{[(2S)-2-hydroxy-3,3-dimethylbutanoyl]amino}-N-{5-[2-phenoxymethyl)phenyl]-1,3-thiazol-2-yl}pentanamide 1.36 g of benzotriazol-1-yloxy-tripyrrolidinephosphonium hexafluorophosphate and 0.7 ml of N-ethylmorpholine are added successively at 0° C. to 0.32 g of (2S)-2-hydroxy-3,3-dimethylbutanoic acid in solution in 25 ml of dimethylformamide. After 20 minutes at 0° C., 0.88 g of (2S)-2-amino-N-(5-{2-[(phenoxy)methyl]phenyl}-1,3-thiazol-2-yl) pentanamide hydrochloride, obtained in step 1.7, is introduced and the mixture is stirred for 18 hours at room temperature. The reaction medium is taken up in ethyl acetate and washed with water. The organic phase is dried over anhydrous sodium sulfate and concentrated. The residue is chromatographed on a silica gel column, eluting with a dichloromethane/methanol 99/1 (v/v) mixture to give, after crystallization from isopropyl ether, 0.83 g of a white solid.

m.p.=84° C.

$^1$H NMR: δ in ppm (DMSO d$_6$): 0.89 (t, 3H); 0.93 (s, 9H); 1.33 (m, 2H); 1.71 (q, 21H); 3.57 (d, 1H); 4.61 (q, 1H); 5.09 (s, 2H); 5.61 (d, 1H); 6.97-7.02 (unresolved complex, 3H); 7.28-7.67 (unresolved complex, 7H); 7.81 (d, 1H); 12.28 (s, 1H).

$[α]_D^{20}$=−81.8 (c=1/CH$_3$OH).

Example 2

Compound No. 16

(2S)-2-{[2-(2,5-dimethyl-3-thienyl)acetyl]amino}-N-{5-[2-(ethoxymethyl)phenyl]-1,3-thiazol-2-yl}pentanamide

2.1 2-(2,5-dimethyl-3-thienyl)-1-(4-morpholinyl)-1-ethanethione 1.68 g of sulfur and 6.5 ml of morpholine are added to 5 g of 2,5-dimethyl-3-acetylthiophene, and the mixture is heated under reflux for 10 hours. The mixture is brought to 20° C. and poured over an aqueous hydrochloric acid solution (1N). The medium is extracted with ethyl acetate. The organic phase is dried over anhydrous sodium sulfate and it is concentrated. The residue is purified by chromatography on a silica gel column, eluting with a cyclohexane/-ethyl acetate 8/2 (v/v) mixture to give 6.8 g of an orange-colored oil.

¹H NMR: δ in ppm (DMSO d₆): 2.30 (2, 3H); 2.34 (s, 3H); 3.47 (t, 2H); 3.65 (m, 4H); 4.07 (s, 2H); 4.20 (t, 2H); 6.56 (s, 1H).

2-(2,5-Dimethyl-3-thienyl)acetic acid 2-(2,5-Dimethyl-3-thienyl)acetic acid is prepared according to a method described in Heterocycl. Chem; EN; 25; 1988; 1571-1581. 21 ml of an aqueous sodium hydroxide solution (50% by mass) are added to 6.7 g of 2-(2,5-dimethyl-3-thienyl)-1-(4-morpholinyl)-1-ethanethione obtained in step 2.1, in solution in 70 ml of methanol, and the mixture is heated for 6 hours under reflux. After evaporation of the methanol, the residue is diluted with water and acidified with an aqueous hydrochloric acid solution (6N). The precipitate formed is filtered and then it is chromatographed on a silica gel column, eluting with dichloromethane to give 3.6 g of beige crystals.

m p.=65° C.

¹H NMR: δ in ppm (DMSO d₆): 2.26 (s, 3H); 2.34 (s, 3H); 3.39 (s, 2H); 6.56 (s, 1H).

2.3 (2S)-2-{[(2,5-Dimethyl-3-thienyl)acetyl]amino}-N-{5-[2-(ethoxymethyl)phenyl]-1,3-thiazol-2-yl}pentanamide The procedure is carried out in the same manner as in step 1.8 of Example 1, replacing (2S)-2-hydroxy-3,3-dimethylbyutanoic acid with 2-(2,5-dimethyl-3-thienyl)acetic acid, obtained in step 2.2. 0.67 g of white crystals is obtained.

m.p.=84° C.

¹H NMR: δ in ppm (DMSO d₆): 0.89 (t, 3H); 1.16 (t, 3H); 1.29 (m, 2H); 1.65 (m, 2H); 2.25 (s, 3H); 2.30 (s, 3H); 3.33 (m, 2H); 3.47 (q, 2H); 4.44 (s, 2H); 4.49 (q, 1H); 4.55 (s, 1H); 7.35-7.55 (unresolved complex, 5H); 8.32 (d, 1H); 12.28 (s, 1H).

$[\alpha]_D^{20}$=−103 (c=1/CH₃OH).

Example 3

Compound No. 22

(2S)-2-{[2-(5-Methyl-2-thienyl)acetyl]amino}-N-{5-[2-(phenoxymethyl)phenyl]-1,3-thiazol-2-yl}pentanamide 3.1 2-(5-Methyl-2-thienyl)-1-(4-morpholinyl)-1-ethanethione 2-(5-Methyl-2-thienyl)-1-(4-morpholinyl)-4-ethanethione is prepared according to a method similar to that described in Example 2.1.

¹H NMR: δ in ppm (DMSO d₆): 2.40 (s, 3H); 3.49 (t, 2H); 3.64 (t, 2H); 3.81 (t, 2H); 4.19 (t, 2H); 4.40 (s, 2H); 6.49 (d, 1H); 6.77 (d, 1H).

3.2 2-(5-Methyl-2-thienyl)acetic acid 2-(5-Methyl-2-thienyl)acetic acid is prepared according to a method similar to that described in Example 2.2.

m.p.=54° C.

¹H NMR: δ in ppm (DMSO d₆): 2.38 (s, 3H); 3.72 (s, 3H); 6.61 (d, 1H); 6.69 (d, 1H).

3.3 (2S)-2-{[2-(5-Methyl-2-thienyl)acetyl]amino}-N-{5-[2-(phenoxymethyl)phenyl]-1,3-thiazol-2-yl}pentanamide The procedure is carried out in the same manner as in step 1.8 of Example 1, replacing (2S)-2-hydroxy-3,3-dimethylbutanoic acid with 2-(5-methyl-2-thienyl)acetic acid, obtained in step 3.2. 0.73 g of beige crystals is obtained.

m.p.=81° C.

¹H NMR: δ in ppm (DMSO d₆): 0.87 (t, 3H); 1.32 (m, 2H); 1.64 (m, 2H); 2.36 (s, 3H); 3.62 (q, 2H); 4.48 (q, 1H); 5.07 (s, 2H); 6.59 (d, 1H); 6.67 (d, 1H); 6.95-7 (unresolved complex, 3H); 7.27-7.73 (unresolved complex, 7H); 8.41 (d, 1H); 12.30 (s, 1H).

$[\alpha]_D^{20}$=−91.7 (c=1/CH₃OH).

Example 4

Compound No. 7

(2S)—N-{5-[2-(Isopropoxymethyl)phenyl]-1,3-thiazol-2-yl}-2-{[3-(3-thienyl)propanoyl]amino}pentanamide 4.1 (E)-3-(3-Thienyl)-2-propenoic acid 46 g of malonic acid and 2 ml of piperidine are added to 25 g of 3-thienaldehyde in solution in 100 ml of pyridine, and the mixture is heated at 100° C. for 4 hours. The reaction medium is cooled to 30° C. and it is poured over an aqueous hydrochloric acid solution (2N). The precipitate formed is filtered and it is rinsed with isopropyl ether to give, after drying, 30 g of a white solid.

m.p.=152° C.

¹H NMR: δ in ppm (DMSO d₆): 6.36 (d, 1H); 7.51-7.62 (unresolved complex, 3H); 7.93 (d, 1H); 12.27 (s, 1H).

4.2 Ethyl (E)-3-(3-thienyl)-2-propenoate 11.5 g of potassium carbonate and 6.8 ml of iodoethane are added to 11 g of (E)-3-(3-thienyl)-2-propenoic acid, obtained in step 4.1, in solution in 50 ml of dimethylformamide, and the mixture is stirred for 48 hours at 20° C. The medium is taken up in ethyl acetate and it is washed with water. The organic phase is dried over anhydrous sodium sulfate and it is concentrated to give 12.5 g of oil.

¹H NMR: δ in ppm (DMSO d₆): 1.26 (t, 3H); 4.17 (q, 2H); 6.47 (d, 1H); 7.57-7.71 (unresolved complex, 3H); 8.01 (d, 1H).

4.3 Ethyl 3-(3-thienyl)-2-propanoate 4 g of 10% palladium on carbon are added to 12.5 g of ethyl (E)-3-(3-thienyl)-2-propenoate, obtained in step 4.2, in solution in 100 ml of ethanol, and the mixture is stirred for 24 hours at 60° C. under 5 bar of hydrogen. The catalyst is filtered and the filtrate is concentrated to give 11 g of oil.

¹H NMR: δ in ppm (DMSO d₆): 1.20 (t, 3H); 2.62 (t, 2H); 2.88 (t, 2H); 4.07 (q, 2H); 7.02 (d, 1H); 7.18 (m, 1H); 7.45 (m, 1H).

4.4 3-(3-Thienyl)propanoic acid 75 ml of an aqueous sodium hydroxide solution (2N) are added to 11 g of ethyl 3-(3-thienyl)-2-propanoate, obtained in step 4.3, in solution in 100 ml of ethanol. The mixture is stirred for 18 hours at 20° C. After evaporation of the solvents, the residue is acidified. The precipitate formed is filtered and dried under vacuum to give 6.3 g of a beige solid.

m.p.=59° C.

$^1$H NMR: δ in ppm (DMSO d$_6$): 2.56 (t, 2H); 2.85 (t, 2H); 7.02 (t, 1H); 7.18 (s, 1H); 7.45 (m, 1H); 12.14 (s, 1H).

4.5 (2S)—N-{5-[2-Isopropoxymethyl)phenyl]-1,3-thiazol-2-yl}-2-{[3-(3-thienyl)propanoyl]amino}pentanamide The procedure is carried out in the same manner as in step 1.8 of Example 1, replacing (2S)-2-hydroxy-3,3-dimethylbutanoic acid with 3-(3-thienyl)-propanoic acid, obtained in step 4.4. 0.75 g of beige crystals is obtained.

m.p.=101° C.

$^1$H NMR: δ in ppm (DMSO d$_6$): 0.87 (t, 3H); 1.13 (d, 6H); 1.33 (m, 2H); 1.62 (m, 2H); 2.48 (t, 2H); 2.82 (t, 2H); 3.67 (m, 1H); 4.45 (s, 2H); 4.54 (q, 1H); 6.98 (d, 1H); 7.12 (d, 1H); 7.35-7.57 (unresolved complex, 6H); 8.21 (d, 1H); 12.26 (s, 1H).

$[α]_D^{20}$=−71 (c=1/CH$_3$OH).

Example 5

(2R)-3-Ethyl-2-hydroxy-N-{(1S)-1-[({5-[2-(phenoxymethyl)phenyl]-1,3-thiazol-2-yl}amino)carbonyl]butyl}-pentanamide (Compound No. 42) and (2S)-3-Ethyl-2-hydroxy-N-{(1S)-1-[({5-[2-(phenoxy-methyl)phenyl]-1,3-thiazol-2-yl}amino)carbonyl]butyl}-pentanamide (Compound No. 43)

5.1 3-Ethyl-2-hydroxypentanoic acid 1.5 ml of trimethylsilyl cyanide are carefully added to a solution of 1.24 ml of 2-ethyl-butyraldehyde in 18 ml of anhydrous dichloromethane, followed by a catalytic quantity of zinc iodide. The reaction medium is stirred for 2 hours at room temperature and then at 60° C. for 3.5 hours. The reaction medium is cooled to 0° C. and 3.5 ml of concentrated hydrochloric acid are added. The reaction medium is stirred for 18 hours at room temperature and then for 1 hour under reflux. After cooling, the reaction mixture is poured into water and extracted twice with 50 ml of ethyl acetate. The combined organic phases are extracted with 100 ml of sodium hydroxide (7.5N) at 4° C. After separation, the aqueous phase is washed with 3 times 50 ml of ethyl acetate. The aqueous phase is acidified with 70 ml of hydrochloric acid (12N) and extracted with 3 times 50 ml of ethyl acetate. The pooled organic phases are dried and the solvent is evaporated.

m.p.=84° C.

5.2 (2R)-3-Ethyl-2-hydroxy-N-{(1S)-1-[({5-[2-(phenoxy-methyl)phenyl]-1,3-thiazol-2-yl}amino)carbonyl]butyl}-pentanamide and (2S)-3-ethyl-2-hydroxy-N-{(1S)-1-[({5-[2-(phenoxymethyl)phenyl]-1,3-thiazol-2-yl}amino)-carbonyl]butyl}pentanamide The procedure is carried out in the same manner as in step 1.8 of Example 1, replacing (2S)-2-hydroxy-3,3-dimethylbutanoic acid with 3-ethyl-2-hydroxypentanoic acid, obtained in step 5.1. 0.78 g of white solid is obtained.

Compound No. 42 (SR)

m.p.=67.4° C.

$^1$H NMR: δ in ppm (DMSO d$_6$): 0.74 (t, 3H); 0.84-0.90 (unresolved complex, 6H); 1.26-1.71 (unresolved complex, 9H); 3.94 (m, 1H); 4.57 (q, 1H); 5.07 (s, 2H); 5.40 (s, 1H); 6.94-6.99 (unresolved complex, 3H); 7.26-7.93 (unresolved complex, 7H); 7.91 (d, 1H); 12.27 (s, 1H).

$[α]_D^{20}$=−41.5 (c=1/CH$_3$OH).

Compound No. 43 (SS)

m.p.=122.5° C.

$^1$H NMR: δ in ppm (DMSO d$_6$): 0.78-0.89 (unresolved complex, 9H); 1.18-1.38 (unresolved complex, 6H); 1.55 (m, 1H); 1.68 (q, 2H); 3.92 (m, 1H); 4.60 (q, 1H); 5.07 (s, 2H); 5.49 (d, 1H); 6.95-7 (unresolved complex, 3H); 7.26-7.62 (unresolved complex, 7H); 7.87 (d, 1H); 12.27 (s, 1H).

$[α]_D^{20}$=−72.6 (c=1/CH$_3$OH).

Example 6

Compound No. 40

(2S)-2-[(2-Hydroxy-3-phenylpropanoyl)amino]-N-{5-[2-(phenoxymethyl)phenyl]-1,3-thiazol-2-yl}pentanamide

6.1 3-Phenyl-2-hydroxypropionic acid

A solution of 0.829 g of sodium nitrite in 4.2 ml of water is added dropwise at 0° C. to a suspension of 1.6 g of phenylalanine in 5.3 ml of sulfuric acid (2.5N). The reaction mixture is stirred for 2 hours at 0° C. and then for 17 hours at room temperature. The reaction mixture is extracted with twice 100 ml of ethyl acetate. The pooled organic phases are washed with 100 ml of a saturated sodium chloride solution in water. 1.2 g of yellow crystals are obtained after drying.

m.p.=97° C.

6.2 2-[(2-Hydroxy-3-phenylpropanoyl)amino]-N-{5-[2-(phenoxymethyl)phenyl]-1,3-thiazol-2-yl}pentanamide The procedure is carried out in the same manner as in step 1.8 of Example 1, replacing (2S)-2-hydroxy-3,3-dimethylbutanoic acid with 3-phenyl-2-hydroxypropionic acid, obtained in step 6.1. 0.8 g of white solid is obtained.

m.p.=86° C.

$^1$H NMR: δ in ppm (DMSO d$_6$): 0.85 (t, 3H); 1.24 (m, 2H); 1.63 (m, 2H); 2.70 (m, 1H); 2.57 (m, 1H); 4.17 (m, 1H); 4.56 (q, 1H); 5.08 (s, 2H); 6.94-7.63 (unresolved complex, 15H); 8.02 (m, 1H); 12.25 (s, 1H).

$[α]^{20}$=−28 (c=1/CH$_3$OH).

Example 7

Compound No. 70

(2S)-2-{[(2S)-2-Hydroxy-3,3-dimethylbutanoyl] amino}-N-(5-{2-[(4-pyridinyloxy)methyl]phenyl}-1,3-thiazol-2-yl)pentanamide

7.1 2-(2-Amino-1,3-thiazol-5-yl)phenylmethanol 70 ml of a 3M aqueous hydrochloric acid solution are added to 29.86 g of 5-[2-(tert-butoxy-methyl)phenyl]-N-diphenylmethylene)-1,3-thiazol-2-amine, prepared according to a method similar to that described in steps 1.1 to 1.4 of Example 1, in solution in 140 ml of methanol, and the mixture is kept at room temperature for 18 hours and then heated under reflux for 4 hours. The methanol is evaporated. The residue is taken up in a 6M aqueous hydrochloric acid solution and extracted with diethyl ether. The aqueous phase is brought to a basic pH while cooling it, and it is extracted with ethyl acetate. The ethyl acetate phase is dried over anhydrous sodium sulfate and concentrated. The residue is concreted with diisopropyl ether to give 6 g of a beige solid.

m.p.=145° C.

7.2 tert-Butyl 5-[2-(hydroxymethyl)phenyl]-1,3-thiazol-2-ylcarbamate 1.17 g of magnesium oxide and 29 ml of a 2M aqueous sodium hydroxide solution are added successively to 6 g of 2-(2-amino-1,3-thiazol-5-yl)-phenylmethanol, obtained in step 7.1, in solution in 80 ml of 1,4-dioxane, followed at 0° C., in portions, by 7.6 g of di-tert-butyl dicarbonate ($BOC_2O$). The mixture is left for 48 hours at room temperature, and then the medium is concentrated, it is taken up in water and it is extracted with ethyl acetate. The organic phase is washed with a 5% potassium hydrogen sulfate solution, it is dried over anhydrous sodium sulfate and it is concentrated. The residue is chromatographed on a silica gel column, eluting with a dichloromethane/methanol 99/1 (V/V) mixture to give 2.3 g of oil which is concreted with diisopropyl ether.

m.p.=180.7° C.

7.3 tert-Butyl 5-{2-[(4-pyridinyloxy)methyl]phenyl}-1,3-thiazol-2-ylcarbamate 4.15 g of diisopropyl azodicarboxylate (DIAD) are added, in portions at 0° C., to 5.24 g of triphenyl-phosphine in solution in 60 ml of tetrahydrofuran. After 30 minutes at about 10° C., 1.96 g of 4-hydroxy-pyridine are added in portions, the mixture is left for 30 minutes at about 10° C. and 4.2 g of tert-butyl 5-[2-(hydroxymethyl)phenyl]-1,3-thiazol-2-ylcarbamate, obtained in step 7.2, are introduced. The mixture is left for 4 days at room temperature. The medium is concentrated, it is taken up in a saturated sodium carbonate solution and extracted with dichloromethane. The organic phase is dried over anhydrous sodium sulfate and it is concentrated. The residue is chromatographed on a silica gel column, eluting with a mixture of increasing polarity dichloromethane/methanol 99/1 (V/V) up to dichloromethane/methanol 90/10 (V/V) to give 1 g of oil.

$^1$H NMR: δ in ppm (DMSO d6): 1.52 (s, 9H); 5.27 (s, 2H); 6.10 (q, 2H); 7.05 (m, 1H); 7.41-7.54 (unresolved complex, 6H); 11.60 (s, 1H).

7.4 5-{2-[(4-Pryidinyloxy)methyl]phenyl}-1,3-thiazolamine 20 ml of a 4M gaseous hydrochloric acid solution in ethyl acetate are added to 1 g of tert-butyl 5-{2-[(4-pyridinyloxy)methyl]phenyl}-1,3-thiazol-2-ylcarbamate, obtained in step 7.3, in 20 ml of dichloromethane. The mixture is left for 4 hours at room temperature. The reaction medium is concentrated and it is brought to a basic pH with a 5% sodium hydrogen sulfate solution. The precipitate formed is filtered and chromatographed on a silica gel column, eluting with a dichloromethane/methanol 95/5 (V/V) mixture to give 0.58 g of a beige foam.

$^1$H NMR: δ in ppm (DMSO d6): 5.25 (s, 2H); 6.10 (d, 2H); 6.98-7.55 (unresolved complex, 9H)

7.5 (2S)-2-{[(2S)-2-hydroxy-3,3-dimethylbutanoyl] amino}-N-(5-{2-[(4-pyridinyloxy)methyl]phenyl}-1,3-thiazol-2-yl)pentanamide The procedure is carried out in the same manner as in steps 1.6 to 1.8 of Example 1, replacing 5-{2-[(phenoxy)methyl]phenyl}-1,3-thiazol-2-amine with 5-{2-[(4-pyridinyloxy)methyl]phenyl}-1,3-thiazolamine, obtained in step 7.4. 0.4 g is obtained in the form of crystals.

m.p.=112.7° C.

$^1$H NMR: δ in ppm (DMSO d6): 0.89 (t, 3H); 0.92 (s, 9H); 1.34 (m, 2H); 1.68 (q, 2H); 3.58 (d, 1H); 4.61 (q, 1H); 5.24 (s, 2H); 5.61 (d, 1H); 6.09 (d, 2H); 7.04 (m, 1H); 7.41-7.53 (unresolved complex, 6H); 7.80 (d, 1H); 12.36 (s, 1H).

Compounds No. 61 ((2S)—N-(5-{2-[(3-cyano-phenoxy)methyl]phenyl}-1,3-thiazol-2-yl)-2-{[(2S)-2-hydroxy-3,3-dimethylbutanoyl]amino}pentanamide) and No. 69 ((2S)—N-(5-{2-[(2-cyanophenoxy)methyl]phenyl}-1,3-thiazol-2-yl)-2-{[(2S)-2-hydroxy-3,3-dimethyl-butanoyl] amino}pentanamide) may be prepared according to the method described in Example 7, replacing 4-hydroxypyridine with 3-cyanophenol or 2-cyanophenol, respectively.

The following table illustrates the chemical structures and the physical properties of a few of the compounds of the invention.

In this table:

m.p. (° C.) represents the melting point of the compound in degrees Celsius;

[$α_D$] (c=1, $CH_3OH$) represents the optical rotation of the compound at the concentration of 1 g/l in methanol;

(S) or (R) in columns "$R_3$" and "$R_5$, $R_5$" indicate the stereochemistry of the asymmetric carbons, carrying $R_3$ or $R_5$ respectively, in formula (I). For the carbon carrying $R_5$, the indication (S) or (R) does not relate to the case where $R_5$ and $R_{5'}$ form together an oxo or amine group.

The compounds described in this table were prepared according to the methods described above.

TABLE (I)

| N° | R₁ | R₃ | R₄ | R₅, R₅' | (aryl group) | m. p. (° C.) | [α_D] (c = 1, CH₃OH) |
|---|---|---|---|---|---|---|---|
| 1. | cyclohexyl-CH₂ | CH₃(CH₂)₂— (S) | H | OH, H (R) | 2-(cyclohexyloxymethyl)phenyl | 120.5 | −51 |
| 2. | cyclohexyl-CH₂ | CH₃(CH₂)₂— (S) | H | OH, H (S) | 2-(cyclohexyloxymethyl)phenyl | 106 | −81.8 |
| 3. | 3-pyridyl-CH₂ | CH₃(CH₂)₂— (S) | H | H, H | 2-(cyclohexyloxymethyl)phenyl | 110 | −109.5 |
| 4. | (CH₃)₂CHCH₂— | CH₃(CH₂)₂— (S) | H | OH, H | 2-(cyclohexyloxymethyl)phenyl | 85 | −62.9 |
| 5. | 3-thienyl-CH₂ | CH₃(CH₂)₂— (S) | CH₃— | H, H | 2-(isopropoxymethyl)phenyl | 72 | −65 |
| 6. | 3-thienyl-CH₂ | CH₃(CH₂)₂— (S) | H | H, H | 2-(isopropoxymethyl)phenyl | 51 | −89 |

TABLE-continued (I)

| N° | R$_1$ | R$_3$ | R$_4$ | R$_5$, R$_5'$ | (structure) | m. p. (° C.) | $[\alpha_D]$ (c = 1, CH$_3$OH) |
|---|---|---|---|---|---|---|---|
| 7. | 3-ethylthiophene | CH$_3$(CH$_2$)$_2$—(S) | H | H, H | 2-(isopropoxymethyl)phenyl | 101 | −71 |
| 8. | 3-methylthiophene | CH$_3$(CH$_2$)$_2$—(S) | H | H, H | 2-(phenoxymethyl)phenyl | 74 | −78.9 |
| 9. | (CH$_3$)$_3$C— | CH$_3$(CH$_2$)$_2$—(S) | H | OH, H (S) | 2-(phenoxymethyl)phenyl | 84 | −81.8 |
| 10. | 2-methylthiophene | CH$_3$CH$_2$—(S) | H | H, H | 2-(phenoxymethyl)phenyl | 76.5 | −100.2 |
| 11. | (CH$_3$)$_3$C— | CH$_3$(CH$_2$)$_2$—(S) | H | OH, H (S) | 2-(isopropoxymethyl)phenyl | 63 | −87 |

TABLE-continued (I)

| N° | R₁ | R₃ | R₄ | R₅, R₅' | [Ar group with C₁₋₄alkylene—X—R₂] | m. p. (° C.) | [α_D] (c = 1, CH₃OH) |
|---|---|---|---|---|---|---|---|
| 12. | 2-thienyl | CH₃(CH₂)₂— (S) | H | H, H | 2-(isopropoxymethyl)phenyl | 62 | −88 |
| 13. | (CH₃)₃C— | CH₃(CH₂)₂— (S) | H | H, H | 2-(isopropoxymethyl)phenyl | 77 | −81 |
| 14. | (CH₃CH₂)(CH₃)CH— | CH₃(CH₂)₂— (S) | H | =O | 2-(isopropoxymethyl)phenyl | 112 | −66 |
| 15. | (CH₃)₃C— | CH₃(CH₂)₂— (S) | H | OH, H (S) | 2-(ethoxymethyl)phenyl | 148 | −87 |
| 16. | 2,5-dimethyl-3-thienyl | CH₃(CH₂)₂— (S) | H | H, H | 2-(ethoxymethyl)phenyl | 84 | −103 |
| 17. | (CH₃)₃C— | CH₃(CH₂)₂— (S) | H | OH, H (S) | 2-((3-(trifluoromethoxy)phenoxy)methyl)phenyl | 114 | −75 |

TABLE-continued
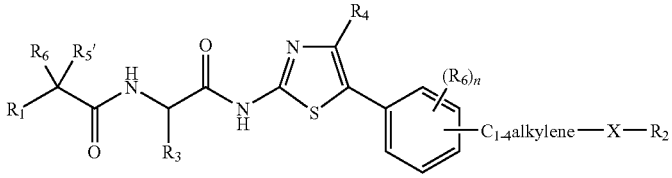
(I)
| N° | R₁ | R₃ | R₄ | R₅, R₅' | 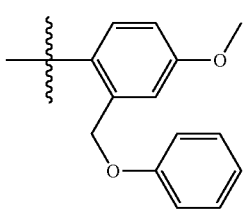 | m. p. (° C.) | $[\alpha_D]$ (c = 1, CH₃OH) |
|---|---|---|---|---|---|---|---|
| 18. | (CH₃)₃C— | CH₃(CH₂)₂— (S) | H | OH, H (S) | 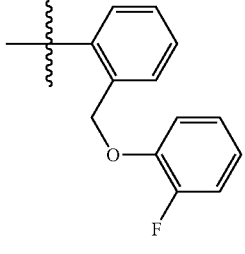 | 117 | −78.3 |
| 19. | (CH₃)₃C— | CH₃(CH₂)₂— (S) | H | OH, H (S) | 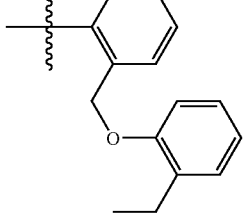 | 92 | −77.7 |
| 20. | (CH₃)₃C— | CH₃(CH₂)₂— (S) | H | OH, H (S) | 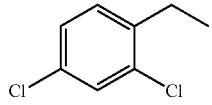 | 107 | −88.7 |
| 21. | 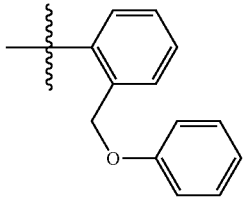 | CH₃(CH₂)₂— (S) | H | H, H | 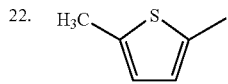 | 82 | −31.3 |
| 22. | 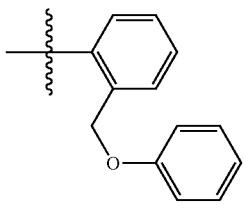 | CH₃(CH₂)₂— (S) | H | H, H |  | 81 | −91.7 |

TABLE-continued (I)

| N° | R₁ | R₃ | R₄ | R₅, R₅' | [structure] | m.p. (°C.) | [α_D] (c=1, CH₃OH) |
|---|---|---|---|---|---|---|---|
| 23. | (CH₃)₃C— | CH₃(CH₂)₂— (S) | H | OH, H (S) | 2-(2,3-dimethoxyphenoxymethyl)phenyl | 99 | −71 |
| 24. | (CH₃)₃C— | CH₃(CH₂)₂— (S) | H | OH, H (S) | 2-(2-trifluoromethoxyphenoxymethyl)phenyl | 66 | −64.4 |
| 25. | (CH₃)₃C— | CH₃(CH₂)₂— (S) | H | OH, H (S) | 2-(3,5-dimethoxyphenoxymethyl)phenyl | 66.5 | −65.4 |
| 26. | (CH₃)₃C— | CH₃(CH₂)₂— (S) | H | OH, H (S) | 2-(2,3-dimethylphenoxymethyl)phenyl | 88 | −80.6 |
| 27. | (CH₃)₃C— | CH₃(CH₂)₂— (S) | H | OH, H (S) | 2-(3,4-dimethylphenoxymethyl)phenyl | 89 | −74.6 |

TABLE-continued

Formula (I): R6-R5'-R1-C(=O)-NH-CHR3-C(=O)-NH-[thiazole with R4 and S]-phenyl(R6)n-C1-4alkylene-X-R2

| N° | R₁ | R₃ | R₄ | R₅, R₅' | (R6)n / C1-4alkylene—X—R2 | m.p. (°C.) | [α_D] (c = 1, CH₃OH) |
|---|---|---|---|---|---|---|---|
| 28. | (CH₃)₃C— | CH₃(CH₂)₂— (S) | H | OH, H (S) | benzyl-O-2,6-dimethylphenyl | 87 | −81.7 |
| 29. | (CH₃)₃C— | CH₃(CH₂)₂— (S) | H | OH, H (S) | benzyl-O-3-chlorophenyl | 169 | −83.5 |
| 30. | (CH₃)₃C— | CH₃(CH₂)₂— (S) | H | OH, H (S) | benzyl-O-3,4-dimethoxyphenyl | 81.5 | −63 |
| 31. | (CH₃)₃C— | CH₃(CH₂)₂— (S) | H | OH, H (S) | benzyl-O-2,6-dimethoxyphenyl | 69.5 | −63.2 |
| 32. | (CH₃)₃C— | CH₃(CH₂)₂— (S) | H | OH, H (S) | benzyl-O-2,4-dimethylphenyl | 86 | −70.5 |

TABLE-continued (I)

[Structure I: R6-R5'-R1 group with NH-C(O)-CH(R3)-NH-C(O)-thiazole(R4)-phenyl(R6)n-C1-4alkylene-X-R2]

[Substituent structure: phenyl(R6)n-C1-4alkylene-X-R2]

| N° | R₁ | R₃ | R₄ | R₅, R₅' | | m.p. (°C.) | [α_D] (c = 1, CH₃OH) |
|---|---|---|---|---|---|---|---|
| 33. | (CH₃)₃C— | CH₃(CH₂)₂— (S) | H | OH, H (S) | benzyl-O-(2,5-dimethylphenyl) on phenyl | 87 | −75.4 |
| 34. | (CH₃)₃C— | CH₃(CH₂)₂— (S) | CH₃— | OH, H (S) | benzyl-O-phenyl on phenyl | 99 | −74.4 |
| 35. | (CH₃)₃C— | CH₃(CH₂)₂— (R) | H | OH, H (S) | benzyl-O-phenyl on phenyl | 78.5 | +46.7 |
| 36. | (CH₃)₃C— | CH₃(CH₂)₂— (S) | H | OH, H (S) | benzyl-O-(2-methylphenyl) on phenyl | 96.5 | −66.7 |
| 37. | (CH₃)₂CH— | CH₃(CH₂)₂— (S) | H | OH, H (R) | benzyl-O-phenyl on phenyl | 141 | −59.6 |

TABLE-continued (I)

| N° | R₁ | R₃ | R₄ | R₅, R₅' | | m. p. (° C.) | [α$_D$] (c = 1, CH₃OH) |
|---|---|---|---|---|---|---|---|
| 38. | (CH₃)₃C— | CH₃(CH₂)₂— (S) | H | OH, H (S) | 2-(2-methoxyphenoxymethyl)phenyl | 85 | −78 |
| 39. | (CH₃)₃C— | CH₃(CH₂)₂— (S) | H | OH, H (R) | 2-(2-ethoxyphenoxymethyl)phenyl | 88 | −74.4 |
| 40. | PhCH₂CH₂— | CH₃(CH₂)₂— (S) | H | OH, H | 2-(phenoxymethyl)phenyl | 86 | −28 |
| 41. | (CH₃)₃C— | CH₃(CH₂)₂— (S) | H | OH, H | 2-(2,6-dichlorophenoxymethyl)phenyl | 126 | −62.5 |
| 42. | (CH₃CH₂)₂CH— | CH₃(CH₂)₂— (S) | H | OH, H (R) | 2-(phenoxymethyl)phenyl | 67.5 | −41.5 |

TABLE-continued
(I)
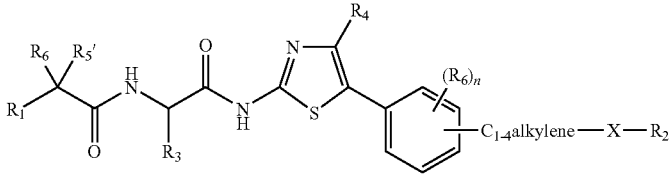
| N° | R$_1$ | R$_3$ | R$_4$ | R$_5$, R$_{5'}$ | | m. p. (° C.) | [α$_D$] (c = 1, CH$_3$OH) |
|---|---|---|---|---|---|---|---|
| 43. | (CH$_3$CH$_2$)$_2$CH— | CH$_3$(CH$_2$)$_2$— (S) | H | OH, H (S) | 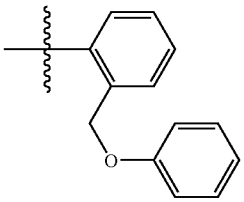 | 122.5 | −72.6 |
| 44. | (CH$_3$)$_3$C— | CH$_3$(CH$_2$)$_2$— (S) | H | OH, H (S) | 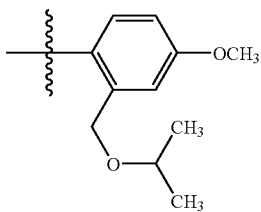 | 79 | −77.9 |
| 45. | (CH$_3$)$_3$C— | CH$_3$(CH$_2$)$_2$— (S) | H | OH, H (S) | 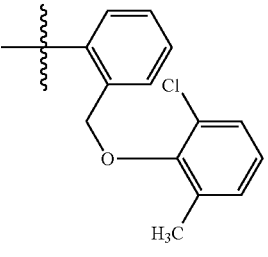 | 96 | −67.3 |
| 46. | (CH$_3$)$_3$C— | CH$_3$(CH$_2$)$_2$— (S) | H | OH, H (S) | 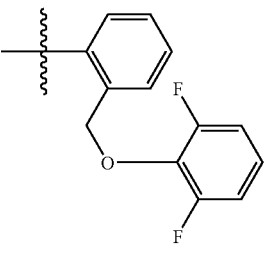 | 63.5 | −75 |
| 47. | (CH$_3$)$_3$C— | CH$_3$(CH$_2$)$_2$— (S) | H | OH, H (S) | 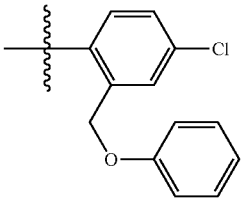 | 93.5 | −80.5 |

TABLE-continued (I)

| N° | R₁ | R₃ | R₄ | R₅, R₅' | (structure) | m. p. (° C.) | [α_D] (c = 1, CH₃OH) |
|---|---|---|---|---|---|---|---|
| 48. | (CH₃)₃C— | CH₃(CH₂)₂— (S) | H | OH, H (S) | 2-(phenoxymethyl)-5-fluorophenyl | 75.5 | −75.3 |
| 49. | (CH₃)₂CH— | CH₃(CH₂)₂— (S) | H | OH, H (S) | 2-(phenoxymethyl)-5-methoxyphenyl | 159.5 | −67.8 |
| 50. | (CH₃)₃C— | CH₃(CH₂)₂— (S) | H | OH, H (S) | 2-((3,4-dichlorophenoxy)methyl)phenyl | — | −72.1 |
| 51. | (CH₃)₂CHCH₂— | CH₃(CH₂)₂— (S) | H | OH, H (S) | 2-((cyclohexyloxy)methyl)phenyl | 158 | −70.2 |
| 52. | (CH₃)₃C— | CH₃(CH₂)₂— (S) | H | OH, H (S) | 4-ethoxy-2-(phenoxymethyl)phenyl | 81 | −75.8 |
| 53. | (CH₃)₂CH— | CH₃(CH₂)₂— (S) | H | OH, H (S) | 4-ethoxy-2-(phenoxymethyl)phenyl | 107.8 | −66.7 |

TABLE-continued (I)

| N° | R₁ | R₃ | R₄ | R₅, R₅' | [Ar group] | m. p. (° C.) | $[\alpha_D]$ (c = 1, CH₃OH) |
|---|---|---|---|---|---|---|---|
| 54. | (CH₃)₃C— | CH₃(CH₂)₂— (S) | H | OH, H (S) | 2-(phenoxymethyl)-4-fluorophenyl | 105.4 | −78.4 |
| 55. | (CH₃)₃C— | CH₃(CH₂)₂— (S) | H | OH, H (S) | 2-(phenoxymethyl)-4-chlorophenyl | 120.7 | −77.2 |
| 56. | (CH₃)₂CH— | CH₃(CH₂)₂— (S) | H | OH, H (S) | 2-(phenoxymethyl)-4-fluorophenyl | 61.4 | −48.6 |
| 57. | (CH₃)₃C— | CH₃(CH₂)₂— (S) | H | OH, H (S) | 2-(cyclohexyloxymethyl)phenyl | 88 | −84.9 |
| 58. | (CH₃)₃C— | CH₃— (S) | H | OH, H (S) | 2-(phenoxymethyl)phenyl | 118.6 | −106.9 |

TABLE-continued (I)

| N° | R₁ | R₃ | R₄ | R₅, R₅' | (aryl group) | m. p. (° C.) | [α$_D$] (c = 1, CH₃OH) |
|---|---|---|---|---|---|---|---|
| 59. | (CH₃)₃C— | CH₃(CH₂)₂— (S) | H | OH, H (S) | 2-methyl-5-(phenoxymethyl)phenyl (CH₃ at 5-position, CH₂OPh at 2-position) | 92.6 | −88.5 |
| 60. | (CH₃)₂CH— | CH₃(CH₂)₂— (S) | H | OH, H (S) | 4-methyl-2-(phenoxymethyl)phenyl | 125.5 | −85 |
| 61. | (CH₃)₃C— | CH₃(CH₂)₂— (S) | H | OH, H (S) | 2-[(3-cyanophenoxy)methyl]phenyl | 162.6 | −104.5 |
| 62. | (CH₃)₃C— | CH₃(CH₂)₂— (S) | H | OH, H (S) | 2-[(3-fluorophenoxy)methyl]phenyl | 160.2 | −71.5 |
| 63. | (CH₃)₂CH— | CH₃(CH₂)₂— (S) | H | OH, H (S) | 2-[(3-fluorophenoxy)methyl]phenyl | 130.7 | −71.6 |

TABLE-continued (I)

| N° | R₁ | R₃ | R₄ | R₅, R₅' | [structure column] | m. p. (° C.) | [α_D] (c = 1, CH₃OH) |
|---|---|---|---|---|---|---|---|
| 64. | (CH₃)₃C— | CH₃(CH₂)₂— (S) | H | OH, H (S) | 2-CH₃ at para, benzyl-O-phenyl | 170 | −78.4 |
| 65. | (CH₃)₂CH— | CH₃(CH₂)₂— (S) | H | OH, H (S) | CH₃ at meta, benzyl-O-phenyl | 135.5 | −72.2 |
| 66. | (CH₃)₃C— | CH₃— (S) | H | OH, H (S) | benzyl-O-cyclohexyl | 104.8 | −108.6 |
| 67. | (CH₃)₃C— | CH₃(CH₂)₂— (S) | H | OH, H (S) | benzyl-O-(2-Cl-5-CH₃-phenyl) | 82 | −72 |
| 68. | (CH₃)₃C— | CH₃(CH₂)₂— (S) | H | OH, H (S) | benzyl-O-(3-CH₃-phenyl) | 80.6 | −64.7 |

TABLE-continued
(I)
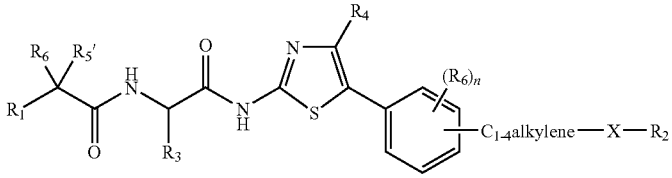
| N° | R$_1$ | R$_3$ | R$_4$ | R$_5$, R$_{5'}$ | 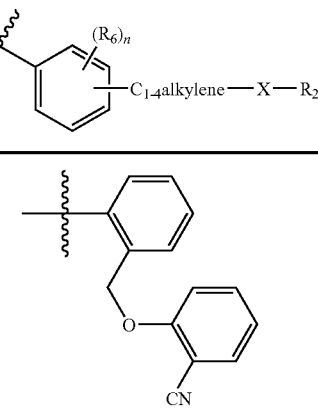 | m. p. (° C.) | [α$_D$] (c = 1, CH$_3$OH) |
|---|---|---|---|---|---|---|---|
| 69. | (CH$_3$)$_3$C— | CH$_3$(CH$_2$)$_2$— (S) | H | OH, H (S) | 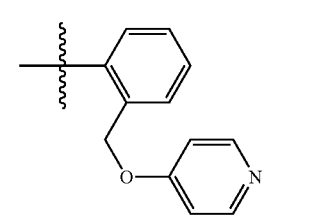 | 99 | −84.6 |
| 70. | (CH$_3$)$_3$C— | CH$_3$(CH$_2$)$_2$— (S) | H | OH, H (S) | | 112.7 | −63.3 |
| 71. | (CH$_3$)$_3$C— | CH$_3$(CH$_2$)$_2$— (S) | H | OH, H (S) | 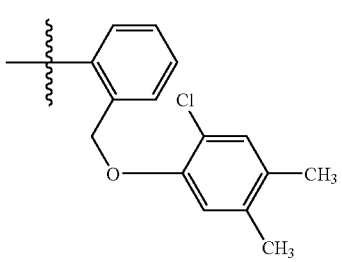 | 85 | −68 |
| 72. | (CH$_3$)$_3$C— | CH$_3$(CH$_2$)$_2$— (S) | H | OH, H (S) | 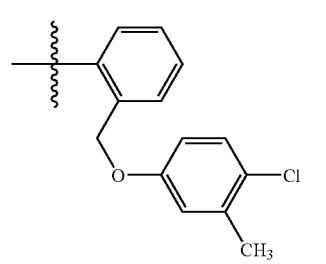 | 83.4 | −56.2 |
| 73. | (CH$_3$)$_3$C— | CH$_3$(CH$_2$)$_2$— (S) | H | OH, H (S) | 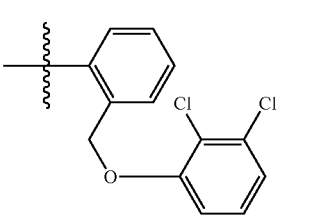 | 71.1 | −69.81 |

TABLE-continued

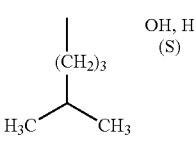

The compounds of the invention have been the subject of pharmacological trials which have shown their value as active substances in therapy.

They have in particular been tested for their β-amyloid peptide (β-A4) production inhibiting effects.

β-Amyloid peptide (β-A4) is a fragment of a larger precursor protein called APP (amyloid precursor protein). The latter is produced and is present in various cells of animal or human tissue. At the cerebral level, its cleavage by protease-type enzymes leads to the formation of the β-A4 peptide which accumulates in the form of an amyloid plaque. The two proteases responsible for the production of the amyloid peptide are known by the name of beta- and gamma-secretases (Wolfe M S, Secretase targets for Alzheimer's disease: identification and therapeutic potential, J. Med. Chem., 2001 Jun. 21; 44(13), 2039-60).

However, it has been demonstrated that this gradual deposition of the β-A4 peptide is neurotoxic and could play an important role in Alzheimer's disease.

Thus, the compounds of the present invention, as inhibitor of the production of β-amyloid peptide (β-A4) by inhibition of gamma-protease, can be used in the treatment of pathologies such as senile dementia, Alzheimer's disease, Down's syndrome, Parkinson's disease, amyloid angiopathy, cerebrovascular disorders, frontotemporal dementia and Pick's disease, post-traumatic dementia, pathologies linked to neuroinflammatory processes, Huntington's disease and Korsakov's syndrome.

The tests were carried out according to the protocol described below.

For the β-amyloid cellular trial, the CHO-K1 line coexpressing the CT100 of APP and PSI M146L clone 30-12 is used. The line targets the inhibition of gamma-secretase. Presenilin is linked to the gamma-secretase activity (Wolfe M S, Haass C., The Role of presenilins in gamma-secretase activity, J. Biol. Chem., 2001 Feb. 23, 276(8), 5413-6) and its coexpression with the amyloid protein or its N-terminal fragment causes an increase in the secretion of the A1-42 peptide (β-A4) thus generating a pharmacological tool which makes it possible to evaluate inhibition by the compounds of formula (I) of the production of the β-A4 peptide. The inoculation of the 96-well culture plates is carried out at the rate of $1 \times 10^5$ cells per well in 150 μl of incubation medium. The presence of a minimum percentage (1.3% final) of serum allows cellular adhesion to the plastic after 2-3 hours of incubation at 37° C., in the presence of 5% $CO_2$. The products (15 μl) are tested at 10 μM DMSO 1% final and are incubated for 24-25 h at 37° C. in the presence of 5% $CO_2$ and of 100% humidity. After this incubation of 24-25 h, the cellular supernatants (100 μl) are transferred to the ELISA plates, treated with the capture antibody 6E10 (6E10, epitope: aal-17, INTERCHIM/SENETEK 320-10), to determine the amount of amyloid peptides secreted by the cells in the presence of compounds according to the invention. A series for a synthetic control peptide, "peptide 1-40", at 5 and 10 ng/ml is treated in parallel. The ELISA plates are incubated overnight at 4° C.

The quantity of bound peptide is detected in an indirect manner in the presence of a competitor corresponding to the truncated peptide, peptide 1-28 coupled to biotin which is then detected with streptavidin coupled to alkaline phosphatase. The substrate, p-Nitrophenyl Phosphate (pNPP FAST p-Nitrophenyl Phosphate, Sigma N2770), gives a yellow soluble reaction product which can be read at 405 nm. The reaction is stopped with a 0.1M EDTA solution. For that, after attachment of the amyloid peptide in the ELISA plate, 50 μl of biotinylated peptide 1-28 are added to 100 μl of cell supernatant and incubated for 30 minutes at room temperature. The ELISA plates are then washed 3 times. After drying by inverting on absorbent paper, 100 μl of streptavidin-Alkaline Phosphatase (Interchim/Jackson ImmunoResearch Laboratories 016-050-084), are added per well and incubated for 1 hour at room temperature. The plates are again washed and then alkaline phosphatase substrate (pNPP 1 mg/ml) is added in an amount of 100 μl per well. After incubating for 30 minutes at room temperature, the reaction is stopped by the addition of 100 μl per well of 0.1M EDTA and the reading is carried out at 405 nm.

The compounds of formula (I) according to the invention showed an EC50 (50% effective concentration) of less than 500 nM. In particular, compound No. 50 in the Table showed an EC50 equal to 295 nM. The compounds for formula (I) according to the invention showed more particularly an EC50 of less than 100 nM.

The results of the biological tests show that the compounds are inhibitors of the formation of the β-amyloid peptide (β-A4).

Thus, these compounds may be used in the treatment of pathologies in which an inhibitor of the formation of the β-amyloid peptide (β-A4) provides a therapeutic benefit. In particular, such pathologies are senile dementia, Alzheimer's disease, Down's syndrome, Parkinson's disease, amyloid angiopathy, cerebrovascular disorders, frontotemporal dementia and Pick's disease, post-traumatic dementia, pathologies linked to neuroinflammatory processes, Huntington's disease and Korsakov's syndrome.

The use of the compounds according to the invention, in the form of base, salt, hydrate or pharmaceutically acceptable solvate, for the preparation of a medicament for treating the abovementioned pathologies forms an integral part of the invention.

The subject of the invention is also medicaments which comprise a compound of formula (I), or an addition salt thereof with a pharmaceutically acceptable acid or alternatively a hydrate or a solvate of the compound of formula (I). These medicaments find their use in therapy, in particular in the treatment of the abovementioned pathologies.

According to another of its aspects, the present invention relates to pharmaceutical compositions containing, as active ingredient, at least one compound according to the invention. These pharmaceutical compositions contain an effective dose of a compound according to the invention, or a pharmaceutically acceptable salt, a hydrate or a solvate of the said compound, and optionally one or more pharmaceutically acceptable excipients.

The said excipients are chosen, according to the pharmaceutical dosage form and the desired mode of administration, from the usual excipients which are known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its optional salt, solvate or hydrate, may be administered in unit form for administration, as a mixture with conventional pharmaceutical excipients, to animals and to human beings for the prophylaxis or the treatment of the above disorders or diseases.

The appropriate unit forms for administration comprise the forms for oral administration such as tablets, soft or hard gelatine capsules, powders, granules, chewing gums and oral solutions or suspensions, the forms for sublingual, buccal, intratracheal, intraocular or intranasal administration or for administration by inhalation, the forms for subcutaneous, intramuscular or intravenous administration and the forms for rectal or vaginal administration. For topical application, the compounds according to the invention may be used in creams, ointments or lotions.

By way of example, a unit form for administration of a compound according to the invention in the form of a tablet can comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

To obtain the desired prophylactic or therapeutic effect, the dose of active ingredient may vary between 0.1 mg and 200 mg per kg of bodyweight and per day. Although these dosages are examples of an average situation, there may be specific cases where higher or lower dosages are appropriate, such dosages also belong to the invention. According to the usual practice, the dosage appropriate for each patient is determined by the doctor according to the mode of administration, the weight and the response of the said patient.

Each unit dose may contain from 0.1 to 1000 mg, preferably from 0.1 to 500 mg, of active ingredient in combination with one or more pharmaceutical excipients. This unit dose may be administered 1 to 5 times per day so as to administer a daily dosage of 0.5 to 5000 mg, preferably of 0.5 to 2500 mg.

The present invention according to another of its aspects also relates to a method for treating the pathologies indicated above which comprises the administration of a compound according to the invention, of a pharmaceutically acceptable salt, of a solvate or of a hydrate of the said compound.

What is claimed is:
1. A method of treating senile dementia, which comprises administering to a patient in need of said treatment an effective amount of a compound of formula I or a pharmaceutically acceptable salt thereof:

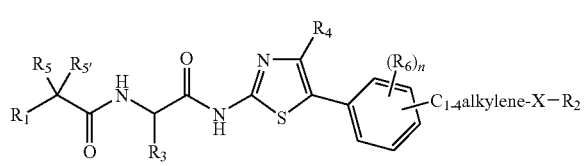

(I)

in which,

X represents an oxygen or sulfur atom;

$R_1$ represents a $C_{1-10}$ alkyl group optionally substituted with a $C_{3-7}$ cycloalkyl, a phenyl or a thienyl; or $R_1$ represents a $C_{3-7}$ cycloalkyl, thienyl, pyridinyl or pyrimidinyl group;

the thienyl groups being optionally substituted with one to three $C_{1-3}$ alkyl groups; the phenyl group being optionally substituted with one to five halogen atoms or $C_{1-3}$ alkyl, $C_{1-3}$ alkoxy, $C_{1-3}$ fluoroalkyl or $C_{1-3}$ fluoroalkoxy groups;

$R_2$ represents a $C_{1-6}$ alkyl group optionally substituted with a $C_{3-7}$ cycloalkyl, phenyl, $C_{1-3}$ alkoxy or hydroxyl group; or $R_2$ represents a $C_{3-7}$ cycloalkyl, piperidinyl, phenyl or pyridinyl group;

the $C_{3-7}$ cycloalkyl and piperidinyl groups being optionally substituted with one or more $C_{1-3}$ alkyl, $C_{1-3}$ alkoxy, hydroxyl, $C_{1-3}$ fluoroalkyl or $C_{1-3}$ fluoroalkoxy groups;

the phenyl and pyridinyl groups being optionally substituted with one or more halogen atoms or $C_{1-3}$ alkyl, $C_{1-3}$ alkoxy, hydroxyl, $C_{1-3}$ fluoroalkyl or $C_{1-3}$ fluoroalkoxy groups;

$R_3$ represents a hydrogen atom or a $C_{1-6}$ alkyl group optionally substituted with a $C_{3-7}$ cycloalkyl group;

$R_4$ represents a hydrogen atom or a $C_{1-6}$ alkyl group;

$R_5$ and $R_{5'}$ represent, independently of each other, a hydrogen or halogen atom, a hydroxyl or $C_{1-3}$ alkyl group; or $R_5$ and $R_{5'}$ form together an oxo or oxime group such as:

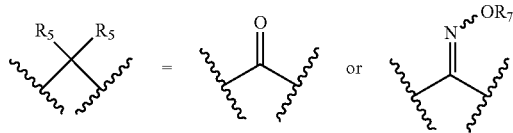

where $R_7$ represents a hydrogen atom or a $C_{1-3}$ alkyl;

n represents an integer ranging from 0 to 3; and $R_6$ represents independently of each other when n=2 or 3, a hydrogen or halogen atom, a hydroxyl, $C_{1-3}$ alkyl, $C_{1-3}$ alkoxy, $C_{1-3}$ fluoroalkyl or $C_{1-3}$ fluoroalkoxy group.

2. The method according to claim 1, wherein:

X represents an oxygen or sulfur atom;

$R_1$ represents a $C_{1-5}$ alkyl group, optionally substituted with a phenyl or a thienyl; or $R_1$ represents a $C_{3-7}$ cycloalkyl group, a thienyl or pyridinyl group; the thienyl groups being optionally substituted with one or two $C_{1-3}$ alkyl groups; the phenyl group being optionally substituted with one or two halogen atoms;

$R_2$ represents a $C_{1-6}$ alkyl, $C_{3-7}$ cycloalkyl, phenyl or pyridinyl group; the phenyl group being optionally substituted with one to three CN, $C_{1-3}$ alkyl, $C_{1-3}$ alkoxy, hydroxyl or fluoroalkoxy groups, or halogen atoms;

$R_3$ represents a $C_{1-6}$ alkyl group;

$R_4$ represents a hydrogen atom or a $C_{1-6}$ alkyl group;

$R_5$ and $R_{5'}$ represent, independently of each other, a hydrogen atom or a hydroxyl; or $R_5$ and $R_{5'}$ form together an oxo group;

$R_6$ represents a hydrogen or halogen atom, a $C_{1-3}$ alkyl or a $C_{1-3}$ alkoxy; and n is 0 or 1.

3. The method according to claim 1, wherein:

X represents an oxygen atom;

$R_1$ represents a methyl, ethyl, 1-methylethyl, 1,1-dimethylethyl, propyl, 1-methylpropyl, 2-methylpropyl or 1-ethylpropyl, optionally substituted with a phenyl or with a thienyl; or $R_1$ represents a cyclohexyl, thienyl or pyridinyl; the thienyl groups being optionally substituted with one or two methyl groups; the phenyl group being optionally substituted with one or two chlorine or fluorine atoms;

$R_2$ represents an ethyl, 1-methylethyl, cyclohexyl, phenyl or pyridinyl group;

the phenyl group being optionally substituted with one to three CN, methyl, ethyl, methoxy, ethoxy, hydroxyl or trifluoromethoxy groups, or chlorine or fluorine atoms;

$R_3$ represents a methyl, ethyl or propyl group;

$R_4$ represents a hydrogen atom or a methyl or 4-methylpentyl group;

$R_5$ and $R_{5'}$ represent, independently of each other, a hydrogen atom or a hydroxyl; or $R_5$ and $R_{5'}$ form together an oxo group;

$R_6$ represents a hydrogen, chlorine or fluorine atom, a methyl, a methoxy or an ethoxy;

n is 0 or 1; and the $C_{1-4}$ alkylene group is a methylene.

* * * * *

UNITED STATES PATENT AND TRADEMARK OFFICE
CERTIFICATE OF CORRECTION

| | | |
|---|---|---|
| PATENT NO. | : 7,879,889 B2 | Page 1 of 1 |
| APPLICATION NO. | : 12/488658 | |
| DATED | : February 1, 2011 | |
| INVENTOR(S) | : Pierre Despey-Roux et al. | |

It is certified that error appears in the above-identified patent and that said Letters Patent is hereby corrected as shown below:

In column 18, line 67, delete "$[\alpha]^{20}$" and insert -- $[\alpha]_D^{20}$ --, therefor.

In column 20, line 60, delete "$R_5$" and insert -- $R_{5'}$ --, therefor.

In column 54, line 5, in claim 2, after "three" delete "CN,".

In column 54, line 28, in claim 3, after "three" delete "CN,".

Signed and Sealed this
Twenty-third Day of August, 2011

David J. Kappos
*Director of the United States Patent and Trademark Office*